United States Patent
McClelland et al.

(10) Patent No.: US 6,696,277 B1
(45) Date of Patent: *Feb. 24, 2004

(54) ARBITRARILY PRIMED POLYMERASE CHAIN REACTION METHOD FOR FINGERPRINTING GENOMES

(75) Inventors: Michael McClelland, Del Mar, CA (US); John T. Welsh, Leucadia, CA (US); Joseph A. Sorge, Rancho Santa Fe, CA (US)

(73) Assignees: Stratagene, La Jolla, CA (US); California Institute of Biological Research, La Jolla, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 08/397,335

(22) Filed: Mar. 1, 1995

Related U.S. Application Data

(60) Division of application No. 07/959,119, filed on Oct. 9, 1992, now Pat. No. 5,487,985, which is a continuation-in-part of application No. 07/633,095, filed on Dec. 21, 1990, now abandoned, which is a continuation-in-part of application No. 07/598,913, filed on Oct. 15, 1990, now abandoned.

(51) Int. Cl.$^7$ .............................. C12P 19/34; C12Q 1/68
(52) U.S. Cl. ......................... 435/91.2; 435/6; 435/91.1
(58) Field of Search .......................... 435/6, 810, 91.1, 435/91.2; 436/501; 536/23.1, 24.1, 24.3–24.33, 25.3; 935/77, 78

(56) References Cited

U.S. PATENT DOCUMENTS

| | | | |
|---|---|---|---|
| 4,683,195 A | | 7/1987 | Mullis et al. ................... 435/6 |
| 4,683,202 A | | 7/1987 | Mullis ......................... 435/91 |
| 4,963,663 A | | 10/1990 | White et al. .................. 536/27 |
| 4,965,188 A | | 10/1990 | Mullis et al. .................. 435/6 |
| 5,043,272 A | | 8/1991 | Hartley ........................ 435/91 |
| 5,104,792 A | | 4/1992 | Silver et al. ................... 435/6 |
| 5,126,239 A | | 6/1992 | Livak et al. ................... 435/6 |
| 5,262,311 A | | 11/1993 | Pardee et al. ............... 435/91.2 |
| 5,487,985 A | * | 1/1996 | McClelland et al. ....... 435/91.2 |

OTHER PUBLICATIONS

Amann et al., "Fluorescent–Oligonucleotide Probing of Whole Cells for Determinative, Phylogenetic, and Environmental Studies in Microbiology," *J. Bact.*, 172:762–770 (1990).

Boerwinkel et al., "Rapid Typing of Tandemly Repeated Hypervariable Loci by the Polymerase Chain Reaction: Application to the Apolipoprotein B 3' Hypervariable Region," *Proc. Natl. Acad. Sci. USA*, 86:212–216 (1989).

DeLong et al., "Phylogenetic Strains: Ribosomel RNA–Based Probes for the Identification of Single Cells," *Science*, 243:1360–1363 (1989).

Eisenach et al., "Repetitive DNA Sequences as Probes for Mycobaterium tuberculosis," *J. Clin. Microbiol.*, 26:2240–2245 (1988).

Goblet et al., "One–Step Amplification of Transcripts in Total RNA Using the Polymerase Chain Reaction," *Nucleic Acids Res.*, 17:2144 (1989).

Jeffreys et al., "Individual–Specific 'Fingerprints' of Human DNA," *Nature*, 316:76–79 (1985).

Julier et al., "Minisatellite Linkage Maps in the Mouse by Cross–Hybridization with Human Probes Containing Tandem Repeats," *Proc. Natl. Acad. Sci. USA*, 87:4585–4589 (1990).

Sommer and Tautz, "Minimal Homology Requirements for PCR Primers," *Nucleic Acids Res.*, 17:6749 (1989).

Welsh et al., "Arbitrarily Primed PCR Fingerprinting of RNA," *Nucleic Acids Res.*, 20:4965–4970 (1992).

Welsh and McClelland, "Fingerprinting Genomes Using PCR With Arbitrary Primers," *Nucleic Acids Res.*, 18:7213–7218 (1990).

Saiki et al., Science, vol. 239, pp. 487–491, 1988.*
Landegren et al., Science, vol. 242, pp. 229–237, 1988.*
Noonan et al. (1988) Nucleic Acids Res., vol. 16, No. 21, p. 10366.
Chelby et al. (1988) Nature, vol. 333, pp. 858–860.

* cited by examiner

*Primary Examiner*—Ardin H. Marschel
(74) *Attorney, Agent, or Firm*—Finnegan, Henderson, Farabow, Garrett & Dunner, LLP

(57) ABSTRACT

A method for generating a discrete set of DNA segments characteristic of a sample of a single-stranded RNA is provided.

3 Claims, 10 Drawing Sheets

ARBITRARILY PRIMED POLYMERASE CHAIN REACTION METHOD FOR FINGERPRINTING GENOMES

This application is a divisional of application Ser. No. 07/959,119, filed Oct. 9, 1992, which issued as U.S. Pat. No. 5,487,985, which is a continuation in part of application Ser. No. 07/633,095, filed on Dec. 21, 1990, which is now abandoned, which is a continuation in part of application Ser. No. 07/598,913, filed on Oct. 15, 1990, which is now abandoned.

FIELD OF THE INVENTION

This invention is directed toward a method of identifying segments of nucleic acid characteristic of a particular genome in an organism by generating a set of discrete DNA amplification products characteristic of the genome. This set of discrete DNA products forms a fingerprint that can be used to identify the genome. The method can also be used to fingerprint a cell type based on differential gene expression in the cell.

BACKGROUND OF THE INVENTION

For many purposes, it is important to be able to identify the genus, species or other taxonomic classification to which an organism belongs, or to be able to identify a tissue type, rapidly and accurately. Such taxonomic identification must be rapid for pathogenic organisms such as viruses, bacteria, protozoa, and multicellular parasites, and assists in diagnosis and treatment of human and animal disease, as well as studies in epidemiology and ecology. In particular, because of the rapid growth of bacteria and the necessity for immediate and accurate treatment of diseases caused by them, it is especially important to have a fast method of identification.

Traditionally, identification and classification of bacterial species has been performed by study of morphology, determination of nutritional requirements or fermentation patterns, determination of antibiotic resistance, comparison of isoenzyme patterns, or determination of sensitivity to bacteriophage strains. These methods are time-consuming, typically requiring at least 48 to 72 hours, often much more. Other more recent methods include the determination of RNA sequences (Woese, in "Evolution in Procaryotes", Schleifer and Stackebrandt, Eds., Academic Press, London, 1986, the use of strain-specific fluorescent oligonucleotides (DeLong et al., Science 243, 1360–1363, 1989; Amann et al., J. Bact. 172, 762–770, 1990), and the polymerase chain reaction (PCR) technique (U.S. Pat. Nos. 4,683,195 and 4,683,202 to Mullis et al.; Mullis & Faloona, Methods Enzymol., 154:335–350, 1987).

DNA markers genetically linked to a selected trait has been commonly used for diagnostic procedures to identify an organism based on the genotype. The DNA markers commonly used are restriction fragment length polymorphisms (RFLPs). Polymorphisms useful in genetic mapping are those polymorphisms that segregate in populations. Traditionally, RFLPs have been detected by hybridization methodology (e.g. Southern blot), but such techniques are time-consuming and inefficient. Alternative methods include assays for polymorphisms using PCR.

The PCR method allows amplification of a selected region of DNA by providing two DNA primers, each of which is complementary to a portion of one strand within the selected region of DNA. These primers are used to hybridize to the separated strands within the region of DNA sought to be amplified, forming DNA molecules that are partially single-stranded and partially double-stranded. The double-stranded regions are then extended by the action of DNA polymerase, forming completely double-stranded molecules. These double-stranded molecules are then denatured and the denatured single strands are rehybridized to the primers. Repetition of this process through a number of cycles results in the generation of DNA strands that correspond in sequence to the region between the originally used primers. Specific PCR primer pairs can be used to identify genes characteristic of a particular species or even strain. PCR also obviates the need for cloning in order to compare the sequences of genes from related organisms, allowing the very rapid construction of phylogenies based on DNA sequence. For epidemiological purposes, specific primers to informative pathogenic features can be used in conjunction with PCR to identify pathogenic organisms.

Although PCR is a very powerful method for amplifying DNA, conventional PCR procedures require the use of at least two separate primers complementary to specific regions of the genome to be amplified. This requirement means that primers cannot be prepared unless the target DNA sequence information is available, and the primers must be "custom built" for each location within the genome of each species or strain whose DNA is to be amplified.

Although the newer methods have advantages over previous methods for genome identification, there is still a need for a rapid, simple method that can be applied to any species for which DNA can be prepared and that does not require reagents that are specific for each species or knowledge of the molecular biology, biochemistry, or DNA sequence of that species. It is also desirable that such a method be capable of identifying a species from a relatively small quantity of biological material. Additionally, it is highly desirable that such a method is also capable of generating polymorphisms useful in genetic mapping, especially of eukaryotes.

In addition to identification of related plant, animal and bacteria species, DNA segments or "markers" may be used to construct human genetic maps for genome analysis. Goals for the present human genome project include the production of a genetic map and an ordered array of clones along the genome. Using a genetic map, inherited phenotypes such as those that cause genetic diseases, can be localized on the map and ultimately cloned. The neurofibromatosis gene is a recent example of this strategy (Xu et al., Cell, 62:599–608, 1990). The genetic map is a useful framework upon which to assemble partially completed arrays of clones. In the short term, it is likely that arrays of human genomic clones such as cosmids or yeast artificial chromosomes (YACs, Burke et al., Science 236:806–812, 1987) will form disconnected contigs that can be oriented relative to each other with probes that are on the genetic map or the in situ map (Lichter et al., Science, 24:64–69, 1990), or both. The usefulness of the contig map will depend on its relation to interesting genes, the locations of which may only be known genetically. Similarly, the restriction maps of the human genome generated by pulsed field electrophoresis (PFE) of large DNA fragments, are unlikely to be completed without the aid of closely spaced markers to orient partially completed maps. Thus, a restriction map and an array of clones covering an entire mammalian genome, for example the mouse genome, is desirable.

Recently, RFLPs that have variable number tandem repeats (VNTRs) have become a method of choice for human mapping because such VNTRs tend to have multiple alleles and are genetically informative because polymorphisms are more likely to be segregating within a family. The production of fingerprints by Southern blotting with VNTRs (Jeffreys et al., *Nature,* 316:76–79, 1985) has proven useful in forensics. There are two classes of VNTRs; one having repeat units of 9 to 40 base pairs, and the other consisting of minisatellite DNA with repeats of two or three base pairs. The longer VNTRs have tended to be in the proterminal regions of autosomes. VNTR consensus sequences may be used to display a fingerprint. VNTR fingerprints have been used to assign polymorphisms in the mouse (Julier et al., *Proc. Natl. Acad. Sci. USA,* 87:4585–4589, 1990), but these polymorphisms must be cloned to be of use in application to restriction mapping or contig assembly. VNTR probes are useful in the mouse because a large number of crosses are likely to be informative at a particular position.

The mouse offers the opportunity to map in interspecific crosses which have a high level of polymorphism relative to most other inbred lines. A dense genetic map of DNA markers would facilitate cloning genes that have been mapped genetically in the mouse. Cloning such genes would be aided by the identification of very closely linked DNA polymorphisms. About 3000 mapped DNA polymorphisms are needed to provide a good probability of one polymorphism being within 500 kb of the gene. To place so many DNA markers on the map it is desirable to have a fast and cost-effective genetic mapping strategy.

BRIEF SUMMARY OF THE INVENTION

Accordingly, the present invention, referred to herein as arbitrarily primed polymerase chain reaction or "AP-PCR", provides a distinctive variation of the PCR technique by employing arbitrary primers. We have unexpectedly found that the use of a single primer used at low stringency hybridization conditions reproducibly generates specific discrete products that can be resolved into a manageable number of individual bands providing a species "fingerprint". We have also found that the method can be extended to provide a fingerprint characteristic of a genotype at the DNA or RNA level.

The AP-PCR method is suitable for the rapid identification and classification of organisms, for the generation of polymorphisms suitable for genetic mapping of eukaryotes, for the identification of tissue and cell types, and for monitoring changes in the state of gene expression of a cell or tissue. Only a small sample of biological material is needed, and knowledge of the molecular biology, biochemistry, or the target DNA sequence to be identified is not required. In addition, reagents specific for a given species are not required.

In general, AP-PCR is a method for generating a set of discrete DNA products ("amplification products") characteristic of a genome by priming target nucleic acid obtained from a genome or from a cellular RNA preparation with at least one single-stranded primer to form primed nucleic acid such that a substantial degree of mismatching, preferably internal mismatching, occurs between the primer and the target nucleic acid. The primed nucleic acid is then amplified by performing at least one cycle of polymerase chain reaction (PCR) amplification to generate DNA amplification products from mismatched primed sites in the genome. A second step of amplification by PCR is then performed using at least one more cycle, and preferably at least 10 cycles, of PCR amplification to generate a set of discrete DNA amplification products characteristic of the genome.

The single-stranded DNA primer is from about 10 to about 50 nucleotide bases in length, more preferably from about 17 to about 40 nucleotide bases in length. It can be of any sequence. The primer can have sequence redundancies reducing the occurrence of mismatches.

Among the possible primers, the following preferred primers can be used:

G-G-A-A-A-C-A-G-C-T-A-T-G-A-C-C-A-T-G-A (SEQ ID NO:2);

G-T-A-A-T-A-C-G-A-C-T-C-A-C-T-A-T-A-G (SEQ ID NO:3);

G-C-A-A-T-T-A-A-C-C-C-T-C-A-C-T-A-A-A-G (SEQ ID NO:4);

C-C-A-G-C-T-C-G-A-C-A-T-G-G-C-A-C-R-T-G-T-A-T-A-C-A-T-A-Y-G-T-A-A-C (SEQ ID NO:5);

G-G-G-G-A-C-T-A-G-T-A-A-A-A-C-G-A-C-G-G-C-C-A-G-T (SEQ ID NO:6);

G-A-G-A-G-G-A-G-A-A-G-G-A-G-A-G-A-G-A-A-R-R-R-R-R (SEQ ID NO:7);or

C-C-G-G-C-A-T-C-G-A-T-R-R-R-R-R-C-G-A-C-G-G-C-C-A-G (SEQ ID NO:8), wherein R is either A or G, and wherein Y is either C or T.

Alternatively, a preferred arbitrarily chosen single-stranded primer can have a sequence of T-G-T-G-T-G at its 3'-terminus, or be about 20 bases in length with a sequence of A-C-G-C-G-C-A-C at its 3'-terminus.

The single-stranded primer can also be a mixture of at least two different or heterogeneous primer sequences. The different sequences can be of the same or different lengths.

In one embodiment of the method, the first cycle of amplification is performed under conditions in which each cycle of polymerase chain reaction amplification includes a step of incubation at a low stringency annealing temperature. The remaining cycles of polymerase chain reaction amplification, preferably at least 10 cycles, are performed under conditions in which each cycle of polymerase chain reaction amplification includes a step of incubation at a high stringency annealing temperature greater than the low stringency annealing temperature.

In an alternative embodiment, to produce a different pattern and raise the resolving power of the method, a second arbitrary primer is included in the same reaction so that amplification of the nucleic acid primed with each of the primers occurs simultaneously.

The annealing temperature in the first cycle is preferably from about 35° C. to about 55° C. The annealing temperature in the remaining cycles is about the melting temperature of the double-stranded DNA formed by annealing, about 35° C. to 65° C. for primers over 15 bases in length. Preferably this temperature is greater than about 55° C., more preferably about 60° C.

The genome to which the AP-PCR method is applied can be a viral genome; a bacterial genome, including Staphylococcus and Streptococcus; a plant genome, including rice, maize, or soybean, or an animal genome, including a human genome. It can also be a genome of a cultured cell line. The cultured cell line can be a chimeric cell line with at least one human chromosome in a non-human background.

The AP-PCR method can be used to identify an organism as a species of a genus of bacteria, for example, Staphylococcus, from a number of different species. Similarly, the method can be used to determine the strain to which an isolate of the genus Streptococcus belongs, by comparing the DNA amplification products produced by AP-PCR for the isolate to the patterns produced from known strains with the same primer.

The AP-PCR method can also be used to verify the assignment of a bacterial isolate to a species by comparing the AP-PCR fingerprint from the isolate with the AP-PCR fingerprints produced by known bacterial species with the same primer. For this application, the primer is chosen to maximize interspecific difference of the discrete DNA amplification products.

The target nucleic acid of the genome can be DNA, RNA or polynucleotide molecules. If the AP-PCR method is used to characterize RNA, the method also preferably includes the step of extending the primed RNA with an enzyme having reverse transcriptase activity to produce a hybrid DNA-RNA molecule, and priming the DNA of the hybrid with an arbitrary single-stranded primer. In this application, the enzyme with reverse transcriptase activity can be avian myeloblastosis virus reverse transcriptase or Moloney leukemia virus reverse transcriptase.

The discrete DNA amplification products produced by the AP-PCR method can be manipulated in a number of ways. For example, they can be separated in a medium capable of separating DNA fragments by size, such as a polyacrylamide or agarose gel, in order to produce a fingerprint of the amplification products as separated bands. Additionally, at least one separated band can be isolated from the fingerprint and reamplified by conventional PCR. The isolated separated band can also be cleaved with a restriction endonuclease. The reamplified fragments can then be isolated and cloned in a bacterial host. These methods are particularly useful in the detection and isolation of DNA sequences that represent polymorphisms differing from individual to individual of a species.

The ability of the AP-PCR method to generate polymorphisms makes it useful, as well, in the mapping and characterization of eukaryotic genomes, including plant genomes, animal genomes, and the human genome. These polymorphisms are particularly useful in the generation of linkage maps and can be correlated with RFLPs and other markers.

The AP-PCR method is suitable for thd identification of bacterial species and strains, including Staphylococcus and Streptococcus species, mammals and plants. The method of the present invention can identify species, cell types or tissues rapidly, using only a small amount of biological material, and does not require knowledge of the nucleotide sequence of other molecular biology of the nucleic acids of the organisms to be identified. The method can also be used to generate detectable polymorphisms for use in genetic mapping of animals and humans, and be used to detect differential gene expression within tissues.

ADVANTAGES OF THE INVENTION

The present invention provides a method with several advantages for identification of bacteria and other biological materials. The method is simple to perform and rapid; results can be obtained in as little as 36 hours when the template nucleic acids are isolated by boiling. Only small samples of material, e.g., nanogram amounts, are needed. The method yields information that allows the differentiation of even closely related species and can be extended to differentiate between subspecies, strains, or even tissues of the same species. The method requires no prior knowledge of any biochemical characteristics, including the nucleotide sequence of the target nucleic acids, of the organism to be identified. Hence, the primers are termed "arbitrary".

Initially, the method requires the use of no species-specific or sequence-specific reagents, because the primer used is completely arbitrarily chosen. Mismatching between the primer DNA and the target nucleic acids is characteristic of the method and is associated with the use of low stringency hybridization conditions during its initial amplification steps. It is advantageous to be able to initiate amplification in the presence of a substantial degree of mismatching because this widens the variety of primers able to initiate amplification on a particular genome.

Additionally, the method possesses the advantage of requiring only one primer sequence for amplification. This reduces the number of reagents required and alleviates the possibility of false results caused by primer artifacts resulting from the hybridization of two separate primers.

The AP-PCR method of the invention can be used to provide identification of other types of organisms, including viruses, fungi, mammals and plants. The method also provides an efficient way of identifying polymorphisms for use in genetic mapping, especially of eukaryotes, including animals, particularly mice and humans. This method has many applications in mammalian population genetics, pathology, epidemiology and forensics.

In addition to genus and species typing, the methods of the invention provide for the identification of tissue, as in tissue typing, and the identification of strain polymorphisms. For example, one could identify the site or tissue of origin of a metastatic tumor, or the stage of the tumor based on diagnostic differential gene expression. In addition, one can supplement histological identification by the ability to identify the tissue being evaluated using the tissue typing methods described herein.

Insofar as cells or tissues respond at the level of gene expression, one can use the present methods to detect changes in the cell or tissue using the present methods. For example, because particular genes respond to a particular agent or treatment, the method will indicate a response to the treatment at the level of differential gene expression. Thus, cells treated with a transforming agent, a growth factor, a cytokine, a mutagen, a viral pathogen and the like agent which alters the cell's gene expression to produce a differential in the expressed RNA can be detected by the present invention.

DETAILED DESCRIPTION OF THE INVENTION

Figure 1:
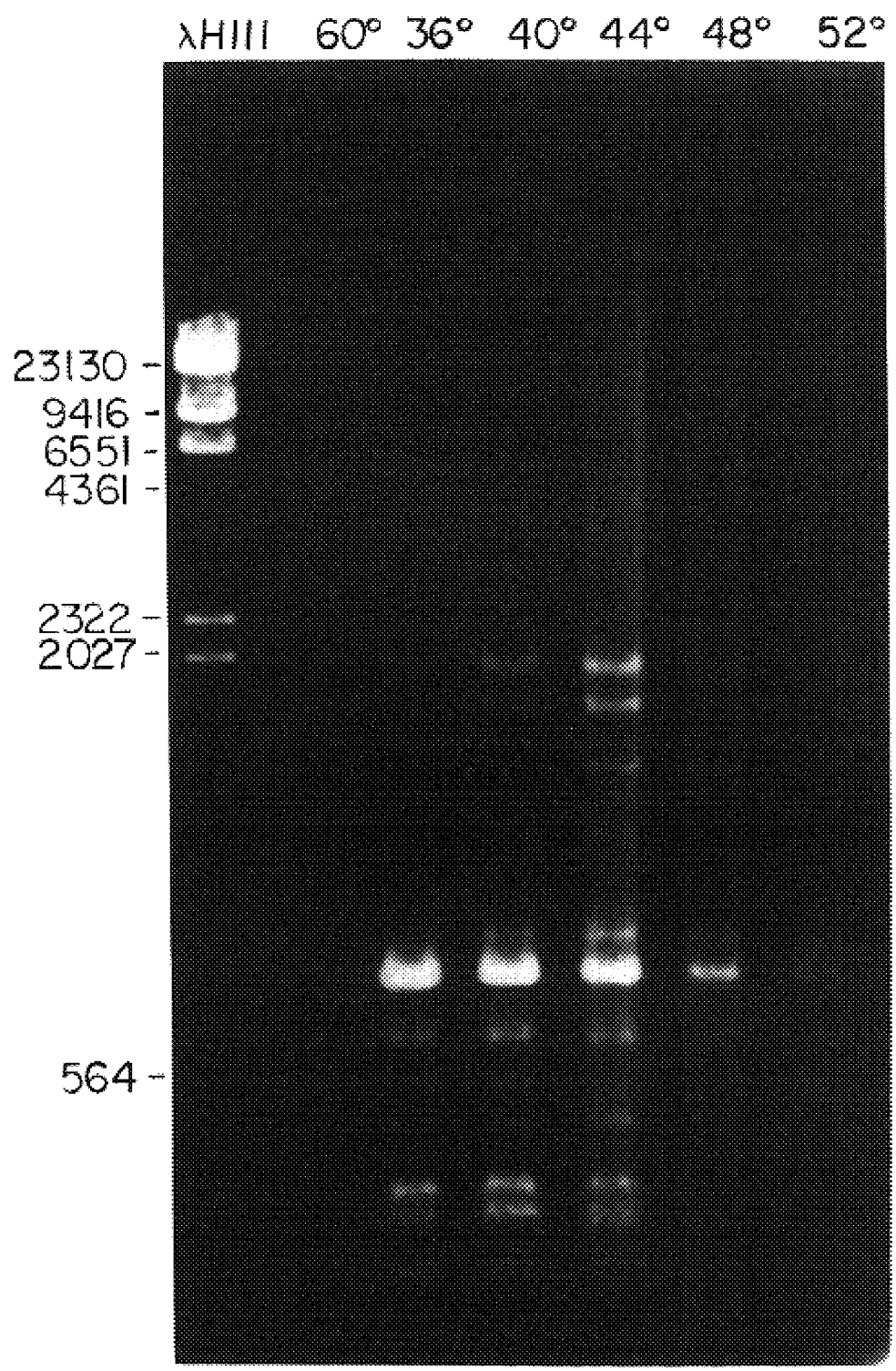
FIG. 1 shows the variation of the AP-PCR pattern produced from *Staphylococcus aureus* ISP8 DNA when the annealing temperature in the first two cycles of PCR is varied, as described in Example 3, infra.

In order that the invention herein described may be more fully understood, the following detailed description is set forth.

This invention relates to a method for generating a set of discrete DNA amplification products characteristic of a genome. This set of discrete DNA amplification products can be resolved by techniques such as gel electrophoresis, producing a distinctive pattern, known as a "fingerprint," that can be used to identify the genome. This method uses a distinctive and novel variation of the polymerase chain reaction (PCR) technique that employs an arbitrary primer and is therefore designated the "arbitrarily primed polymerase chain reaction" ("AP-PCR") method.

In general, the method of the invention involves the following steps:

(1) rendering target nucleic acids of the genome accessible to priming;

(2) priming the target nucleic acids of the genome with an arbitrarily selected single-stranded primer to form primed nucleic acids under hybridization conditions compatible with arbitrarily priming of the target nucleic acids;

(3) performing a number of cycles of PCR on the primed nucleic acids to generate a set of discrete amplification products; and (4) if the discrete DNA amplification products are to be used for the identification of a genome, comparing the amplification products with those produced from nucleic acids obtained from genomes of known species.

Alternatively, the amplification products produced by the invention can be used to assemble genetic maps for genome analysis.

Each of these steps is discussed in detail below.

I. The General Method

A. Selection of Genome

The method of the present invention is particularly well suited to the generation of discrete DNA amplification products from nucleic acids obtained from genomes of all sizes from $5 \times 10^4$ nucleotide bases (viruses) to $3 \times 10^9$ bases and greater (animals and plants).

"Nucleic acids" as that term is used herein means that class of molecules including single-stranded and double-stranded deoxyribonucleic acid (DNA), ribonucleic acid (RNA) and polynucleotides.

The AP-PCR method can be applied to such economically important plants as rice, maize, and soybean. It can also be applied to the genome of any organism, to the genome of a cultured cell line of a tissue or organ, or a genome present in a sample of tissue or organ. The cultured cell line can be chimeric with at least one human chromosome in an otherwise non-human background. The non-human background can be rodent, such as mouse or Chinese hamster.

As described in the Examples, the DNA amplification products can be used to determine that the genome in an unidentified sample of an organism, tissue or cell line belongs to a known genus, type, species or differentiated tissue, thereby identifying the genome. For example, the DNA amplification products produced from a bacterium can be identified to belong to the genus Staphylococcus and can be used further to determine to which species and/or strain of that genus the organism belongs.

B. Rendering the Nucleic Acids of the Genome Accessible to Priming

"Genomic DNA" is used in an art recognized manner to refer to a population of DNA that comprises the complete genetic component of a species. Thus genomic DNA comprises the complete set of genes present in a preselected species. The complete set of genes in a species is also referred to as a genome. Depending on the species, genomic DNA can vary in complexity, and in number of nucleic acid molecules. In higher organisms, genomic DNA is organized into discrete nucleic acid molecules (chromosomes).

For species low in the evolutionary scale, such as bacteria, viruses, yeast, fungi and the like, a genome is significantly less complex than for a species high in the evolutionary scale. For example, whereas E. coli is estimated to contain approximately $2.4 \times 10^9$ grams per mole of haploid genome, man contains about $7.4 \times 10^{12}$ grams per mole of haploid genome.

Genomic DNA is typically prepared by bulk isolation of the total population of high molecular weight nucleic acid molecules present in a biological material derived from a single member of a species. Genomic DNA can be prepared from a tissue sample, from a whole organism or from a sample of cells derived from the organism.

Exemplary biological materials for preparing mammalian genomic DNA include a sample of blood, muscle or skin cells, tissue biopsy or cells cultured from tissue, methods for isolating high molecular weight DNA are well known. See, for example, Maniatis et al., in *Molecular Cloning: A Laboratory Manual*, Cold Spring Harbor Laboratory, N.Y. (1982); and U.S. Pat. No. 4,800,159 to Mullis et al.

Rendering the nucleic acids of the genome accessible to priming requires that the nucleic acids be available for base-pairing by primers and that DNA polymerases and other enzymes that act on the primer-template complex can do so without interference. The nucleic acids must be substantially free of protein that would interfere with priming or the PCR process, especially active nuclease, as well as being substantially free of nonprotein inhibitors of polymerase action such as heavy metals.

A number of methods well-known in the art are suitable for the preparation of nucleic acids in a condition accessible to priming. Typically, such methods involve treatment of cells or other nucleic acid-containing structures, such as virus particles, with a protease such as proteinase K or pronase and a strong detergent such as sodium dodecyl sulfate ("SDS") or sodium lauryl sarcosinate ("Sarkosyl") to lyse the cells. This is followed by extraction with phenol and chloroform to yield an aqueous phase containing the nucleic acid. This nucleic acid is then precipitated with ethanol and redissolved as needed. (See Example 1, infra).

Alternatively, as where the genome is in bacteria, a small portion (~0.5 mm$^2$) of a single bacterial colony can be removed with a 200-µL automatic pipette tip and suspended in 5 µL of TE (0.01 M Tris-HCl, pH 8.0, 1 mM EDTA) in a plastic microfuge tube and boiled for 5 minutes. After the sample is boiled, the debris is pelleted by centrifugation. The AP-PCR method can then be performed directly on the nucleic acids present in the supernatant sample after appropriate dilution.

In some applications, it is possible to introduce samples such as blood or bacteria directly into the PCR protocol as described below without any preliminary step because the first cycle at 94° C. bursts the cells and inactivates any enzymes present.

C. Priming the Target Nucleic Acids
1. The Primer Sequence
a. General Considerations The sample of target nucleic acids is primed with a single-stranded primer. Individual single-stranded primers, pairs of single-stranded primers or a mixture of single-stranded primers can be used.

The primer is completely "arbitrary" in that it can be chosen without knowledge of the sequence of the target nucleic acids to be amplified. The term arbitrary is not to be confused with "random" which connotes a primer composed of a random population of primers each of different and random sequence.

Although the sequence of the primer is arbitrary in sequence with respect to the nucleic acids to be amplified, the sequence of an arbitrary primer is known, not random, and some guidelines to primer selection are found in Innis and Gelfand, "Optimization of PCRs," in *PCR Protocols: A Guide to Methods and Applications*, M. A. Innis, D. H. Gelfand, J. J. Sninsky and T. J. White, eds., Academic Press, New York, 1990, pp. 3–12, incorporated herein by this reference. Briefly, the primer typically has 50 to 60% G+C composition and is free of runs of three or more consecutive C's or G's at the 3'-end or of palindromic sequences, although having a (G+C)-rich region near the 3'-end may be desirable. These guidelines, however, are general and intended to be nonlimiting. Additionally, in many applications it is desirable to avoid primers with a T at the 3' end because such primers can prime relatively efficiently at mismatches, creating a degree of mismatching greater than desired, and affect the background amplification.

The AP-PCR method is based on the rationale that at a sufficiently low hybridization stringency, such as low temperature, primers can be expected to anneal to many genomic sequences with a variety of mismatches. Some of these will be within a few hundred base pairs of each other and on opposite strands. Sequences between these positions will be PCR-amplifiable by virtue of their placement in opposite directions on the genomic double-stranded nucleic acid molecule. The extent to which sequences amplify will depend on the efficiency of priming at each pair of primer annealing sites. Because the sequence of the primer is arbitrarily selected with respect to the target nucleic acid sequence of the genome, a substantial degree of mismatching between the DNA strands of the primer and the target nucleic acids of the genome is expected to occur.

"Substantial degree of mismatching" is defined herein such that at least 6.5% of the nucleotide bases of a primer sequence are paired with inappropriate (non-complementary) bases in the target nucleic acid, e.g. a guanine base in the primer is paired with an adenine base in the target nucleic acid.

As used herein, the phrase "internal mismatching" in its various grammatical forms refers to non-complementary nucleotide bases in the primer, relative to a template to which it is hybridized, that occur between the 5'-terminal most and 3'-terminal most bases of the primer that are complementary to the template. Thus, 5'-terminal and/or 3'-terminal non-complementary bases are not "internally mismatched" bases. A "substantial degree of internal mismatching" is such that at least 6.5% of the nucleotide bases of the primer sequence are paired with inappropriate bases in the target nucleic acid.

In the AP-PCR method of the invention the genome may be primed with a single arbitrary primer, a combination of two or more primers or a mixture of heterogeneous primers, each individual primer in the mixture having a different, but related sequence. When a mixture of primers is used, some, but not all, of the primers can match more efficiently. An example of use of a mixture of primers is provided in Example 11, infra using the primer Kpn-R.

Preferably, the arbitrary primer is about 10 to about 50 nucleotide bases long, and more preferably, about 17 to about 40 bases long. In principle, the shorter the oligonucleotide, the more perfect a match must be in order to permit priming.

Preferably, both the template and the primer are DNA. The template can also be single-stranded RNA molecules, for example messenger RNA, in which case an enzyme with reverse transcriptase activity, such as avian myeloblastosis virus (AMV) reverse transcriptase or Moloney murine leukemia virus (Mo-MLV) reverse transcriptase, is used to generate a hybrid DNA-RNA molecule with an arbitrary primer or a poly T primer. The DNA strand of this hybrid DNA-RNA molecule is then used as the starting material for AP-PCR. Alternatively, the primer can also be a single-stranded ribonucleotide of the appropriate length, which is extended at its 3'-hydroxyl terminus by reverse transcriptase, forming a double-stranded molecule in which one strand is partially DNA and partially RNA.

b. Particular Primer Sequences

Among suitable primers for use in the AP-PCR method of the invention are the primer Kpn-R with the sequence of C-C-A-G-C-T-C-G-A-C-A-T-G-G-C-A-C-R-T-G-T-A-T-A-C-A-T-A-Y-G-T-A-A-C (34 bases) (SEQ ID NO:5), in which R is a purine nucleotide, either A or G, and Y is a pyrimidine nucleotide, either C or T; universal M13, with the sequence of G-G-A-A-A-C-A-G-C-T-A-T-G-A-C-C-A-T-G-A (20 bases) (SEQ ID NO:2); a second M13 sequencing primer, with the sequence of G-G-G-G-A-C-T-A-G-T-A-A-A-A-C-G-A-C-G-G-C-C-A-G-T (25 bases) (SEQ ID NO:6), and primers based on this sequence but progressively truncated at the 5' end; M13 reverse sequencing primer, with the sequence of G-T-A-A-T-A-C-G-A-C-T-C-A-C-T-A-T-A-G (19 bases) (SEQ ID NO:3); a bacteriophage T7 sequencing primer, with the sequence of G-C-A-A-T-T-A-A-C-C-C-T-C-A-C-T-A-A-A-G (20 bases) (SEQ ID NO:4); a T3 sequencing primer, with the sequence of T-T-G-T-A-A-A-A-C-G-A-G-G-C-C-A-G-T (18 bases) (SEQ ID NO:1); and more highly degenerate primers such as a pUC sequencing primer with a sequence of C-C-G-G-C-A-T-C-G-A-T-R-R-R-R-R-R-C-G-A-C-G-G-G-C-A-G (27 bases) (SEQ ID NO:9) and a primer with a sequence of G-A-G-A-G-G-A-G-A-A-G-G-A-G-A-A-G-A-A-R-R-R-R-R (25 bases) (SEQ ID NO:7). These primers are generally of universal application except for Kpn-R, which is not suitable for use with human DNA because it hybridizes with a commonly-occurring dispersed repeating sequence in human DNA. Some of these primers are already commercially available and are in extensive use for other purposes. In addition, these primers may be produced by known techniques, for example by chemical synthesis.

Still other examples of suitable primers include a primer of about 20 bases in length with a sequence of A-C-G-C-G-C-A-C at its 3'-terminus, which may be especially desirable in generating fingerprints that reveal polymorphisms because of the mutability of the CpG dinucleotide. Another primer useful for revealing polymorphisms is a primer with a sequence of T-G-T-G-T-G at its 3'-terminus. This primer should prime at microsatellite repeats such as the dispersed simple repeat $(GT:CA)_n$.

c. Use of Mixtures of Primers

As discussed above, mixtures of heterogeneous primers can also be used, with each primer in the mixture having a different, but related sequence. An example of such a primer is the Kpn-R primer with two degenerate positions. Another example is: G-A-G-A-G-G-A-G-A-A-G-G-A-G-A-G-G-G-A-A-R-R-R-R-R-R (SEQ ID NO:10), where R is either A or G. The individual primers in the mixture can all be the same length. Preferably, primers are constructed to avoid self-priming internally and the creation of artifacts.

Combinations of two or more individual primers can also be used. When such combinations of primers are used, the primers are used simultaneously in the same AP-PCR reaction. These combinations provide a very different pattern from that produced by each primer alone. Surprisingly, the patterns are not more complex. When a number of primers are used in combinations, the number of different patterns resulting is approximately equal to the square of the number of separate primers used divided by two. Therefore, a combination of primers provides more fingerprints than could be generated by using each individual primer alone. When primers are used in such combinations, only primer pairs that do not produce a primer artifact can be used.

2. Concentration of Primer and Template

The quantity of the nucleic acid genome used in the AP-PCR amplification depends on the complexity of the particular genome used. Simple genomes, such as bacterial genomes have a genome size of less than about 5 million base pairs (5 megabases). Complex genomes, such as *sativa* species (rice) have a genome size of about 700–1000 megabases. Other complex genomes such as maize or humans have a genome size of about 3000 megabases.

The amount of simple genome nucleic acid used as template is from about 10 pg to about 250 ng, preferably from about 30 pg to about 7.5 ng. Most preferred is an amount of simple genome nucleic acid template of about 1 ng.

The amount of nucleic acid of a complex genome used as a template is from about 250 ng to about 0.8 ng. More preferably, the amount of nucleic acid of a complex genome used as template is from about 51 ng to about 0.8 ng. Most preferred, are amounts complex genome nucleic acid template of about 50 ng to about 10 ng.

The priming step is carried out as part of the PCR amplification process, and the conditions under which it is performed are discussed below under "Performance of PCR."

D. Performance of PCR

In one embodiment, the present invention utilizes an amplification method where the single-stranded template is hybridized with a primer or primers to form a primer-template hybridization product or products. A hybridization reaction admixture is prepared by admixing effective amounts of a primer, a template nucleic acid and other components compatible with a hybridization reaction. Templates of the present methods can be present in any form, with respect to purity and concentration, compatible with the hybridization reaction.

The hybridization reaction mixture is maintained under hybridizing conditions for a time period sufficient for the primer(s) to hybridize to the templates to form a hybridization product, i.e., a complex containing primer and template nucleic acid strands.

The phrase "hybridizing conditions" and its grammatical equivalents, when used with a maintenance time period, indicates subjecting the hybridization reaction admixture, in the context of the concentrations of reactants and accompanying reagents in the admixture, to time, temperature and pH conditions sufficient to allow the primer(s) to anneal with the template, typically to form a nucleic acid duplex. Such time, temperature and pH conditions required to accomplish hybridization depend, as is well known in the art, on the length of the primer to be hybridized, the degree of complementarity between the primer and the template, the guanidine and cytosine content of the polynucleotide, the stringency of hybridization desired, and the presence of salts or additional reagents in the hybridization reaction admixture as may affect the kinetics of hybridization. Methods for optimizing hybridization conditions for a given hybridization reaction admixture are well known in the art.

Hybridization conditions can be high stringency, which favor exact matches in the annealing of the primer to the target nucleic acids, or can be selected as to be compatible with arbitrary priming of the target nucleic acids, which is described further herin.

The term "primer" as used herein refers to a polynucleotide, whether purified from a nucleic acid restriction digest or produced synthetically, which is capable of acting as a point of initiation of synthesis when placed under conditions in which synthesis of a primer extension product which is complementary to a template is induced, i.e., in the presence of nucleotides and an agent for polymerization such as DNA polymerase, reverse transcriptase and the like, and at a suitable temperature and pH.

The primer must be sufficiently long to prime the synthesis of extension products in the presence of the agents for polymerization. The exact lengths of the primers will depend on many factors, including temperature and the source of primer. For example, depending on the complexity of the template sequence, a polynucleotide primer typically contains from about 8 to about 30 or more nucleotides, although it can contain fewer nucleotides. As few as 8 nucleotides in a polynucleotide primer have been reported as effective for use. Studier et al., *Proc. Natl. Acad. Sci. USA*, 86:6917–21 (1989). Short primer molecules generally require lower temperatures to form sufficiently stable hybridization complexes with template to initiate primer extension.

In some cases, the primers used herein are selected to be "substantially" complementary to the different strands of each specific sequence to be synthesized or amplified. This means that the primer must contain at its 3' terminus a nucleotide sequence sufficiently complementary to nonrandomly hybridize with its respective template. Therefore, the primer sequence may not reflect the exact sequence of the template. For example, a non-complementary polynucleotide can be attached to the 5' end of the primer, with the remainder of the primer sequence being substantially complementary to the strand. Such noncomplementary polynucleotides might code for an endonuclease restriction site or a site for protein binding. Alternatively, noncomplementarity bases or longer sequences can be interspersed into the primer, provided the primer sequence has sufficient complementarity with the sequence of the strand to be synthesized or amplified to non-randomly hybridize therewith and thereby form an extension product under polynucleotide synthesizing conditions.

Sommer et al., *Nuc. Acid Res.*, 17:6749 (1989), reports that primers having as little as a 3 nucleotide exact match at the 3' end of the primer were capable of specifically initiating primer extension products, although less nonspecific hybridization occurs when the primer contains more nucleotides at the 3' end having exact complementarity with the template sequence. Therefore, a substantially complementary primer as used herein must contain at its 3' end at least 3 nucleotides having exact complementarity to the template sequence. A substantially complementary primer preferably contains at least 8 nucleotides, more preferably at least 18 nucleotides, and still more preferably at least 24 nucleotides, at its 3' end having the aforementioned complementarity. Still more preferred are primers whose entire nucleotide sequence has exact complementarity with the template sequence.

The choice of a primer's nucleotide sequence depends on factors such as the distance from the region coding for the desired specific nucleic acid sequence present in a nucleic acid of interest and its hybridization site on the nucleic acid relative to any second primer to be used.

The primer is preferably provided in single-stranded form for maximum efficiency, but may alternatively be double-stranded. If double-stranded, the primer is first treated to separate its strands before being used to prepare extension products. Preferably, the primer is an oligodeoxyribonucleotide.

Primers can be prepared by a variety of methods including de novo chemical synthesis and derivation of nucleic acid fragments from native nucleic acid sequences existing as genes, or parts of genes, in a genome, plasmid, or other vector, such as by restriction endonuclease digest of larger double-stranded nucleic acids and strand separation or by enzymatic synthesis using a nucleic acid template.

De novo chemical synthesis of a primer can be conducted using any suitable method, such as, for example, the phosphotriester or phosphodiester methods. See Narang et al., *Meth. Enzymol.*, 68:90 (1979); U.S. Pat. No. 4,356,270; Itakura et al., *Ann. Rev. Biochem.*, 53:323–56 (1989); and Brown et al., *Meth. Enzymol.*, 68:109 (1979).

Derivation of a primer from nucleic acids involves the cloning of a nucleic acid into an appropriate host by means of a cloning vector, replication of the vector and therefore multiplication of the amount of the cloned nucleic acid, and then the isolation of subfragments of the cloned nucleic acids. For a description of subcloning nucleic acid fragments, see Maniatis et al., *Molecular Cloning: A Laboratory Manual*, Cold Spring Harbor Laboratory, pp 390–401 (1982); and see U.S. Pat. Nos. 4,416,988 and 4,403,036.

The primed template is used to produce a strand of nucleic acid having a nucleotide sequence complementary to the template, i.e., a template-complement.

The template is subjected to a first primer extension reaction by treating (contacting) the template with a (first) primer. The primer is capable of initiating a primer extension reaction by non-randomly hybridizing to a template nucleotide sequence, preferably at least about 8 nucleotides in length and more preferably at least about 20 nucleotide in length. This is accomplished by mixing an effective amount of the primer with the template and an effective amount of nucleic acid synthesis inducing agent to form a primer extension reaction admixture. The admixture is maintained under polynucleotide synthesizing conditions for a time period, which is typically predetermined, sufficient for the formation of a primer extension reaction product.

The primer extension reaction is performed using any suitable method. Generally polynucleotide synthesizing conditions are those wherein the reaction occurs in a buffered aqueous solution, preferably at a pH of 7–9, most preferably about 8. Preferably, a molar excess (for genomic nucleic acid, usually about $10^6$:1 primer:template) of the primer is admixed to the buffer containing the template strand. A large molar excess is preferred to improve the efficiency of the process. For polynucleotide primers of about 20 to 25 nucleotides in length, a typical ratio is in the range of 50 ng to 1 ug, preferably 250 ng, of primer per 100 ng to 500 ng of mammalian genomic DNA.

The deoxyribonucleotide triphosphates (dNTPs) dATP, dCTP, dGTP, and dTTP are also admixed to the primer extension reaction admixture in amounts adequate to support the synthesis of primer extension products, and depends on the size and number of products to be synthesized. The resulting solution is heated to about 90° C.–100° C. for about 1 to 10 minutes, preferably from 1 to 4 minutes. After this heating period the solution is allowed to cool to room temperature, which is preferable for primer hybridization. To the cooled mixture is added an appropriate agent for inducing or catalyzing the primer extension reaction, and the reaction is allowed to occur under conditions known in the art. The synthesis reaction may occur at from room temperature up to a temperature above which the inducing agent no longer functions efficiently. For example, if DNA polymerase is used as inducing agent, the temperature is generally no greater than about 40° C. unless the polymerase is heat-stable.

The inducing agent may be any compound or system which will function to accomplish the synthesis of primer extension products, including enzymes. Suitable enzymes for this purpose include, for example, *E. coli* DNA polymerase I, Klenow fragment of *E. coli* DNA polymerase I, T4 DNA polymerase, T7 DNA polymerase, recombinant modified T7 DNA polymerase described by Tabor et al., U.S. Pat. Nos. 4,942,130 and 4,946,786, other available DNA polymerases, reverse transcriptase, and other enzymes, including heat-stable enzymes, which will facilitate combination of the nucleotides in the proper manner to form the primer extension products which are complementary to each nucleic acid strand.

Heat-stable DNA polymerases are particularly preferred as they are stable in a most preferred embodiment in which PCR is conducted in a single solution in which the temperature is cycled. Representative heat-stable polymerases are the DNA polymerases isolated from *Bacillus stearothermophilus* (Bio-Rad), *Thermus thermophilous* (FINZYME, ATCC #27634), Thermus species (ATCC #31674), *Thermus aquaticus* strain TV 11518 (ATCC #25105), *Sulfolobus acidocaldarius*, described by Bukhrashuili et al, *Biochem. Biophys. Acta,* 1008: 102–7 (1909) and by Elie et al, *Biochem. Biophys. Acta,* 951:261–7 (1988), and *Thermus filiformis* (ATCC #43280). Particularly preferred is Taq DNA polymerase available from a variety of sources including Perkin-Elmer-Cetus, (Norwalk, Conn.), Promega (Madison, Wis.) and Stratagene (La Jolla, Calif.), and AmpliTaq™ DNA polymerase, a recombinant *Thermus aquaticus* Taq DNA polymerase available from Perkin-Elmer-Cetus and described in U.S. Pat. No. 4,889,818.

Generally, the synthesis will be initiated at the 3' end of each primer and proceed in the 5' direction along the template strand, until synthesis terminates, producing molecules of different lengths. There may be inducing agents, however, which initiate synthesis at the 5' end and proceed in the above direction, using the same process as described above.

The primer extension reaction product is then subjected to a second primer extension reaction by treating it with a second polynucleotide primer having a preselected nucleotide sequence. The second primer is capable of initiating the second reaction by hybridizing to a nucleotide sequence, preferably at least about 8 nucleotides in length and more preferably at least about 20 nucleotides in length, found in the first product. This is accomplished by mixing the second primer, preferably a predetermined amount thereof, with the first reaction product, preferably a predetermined amount thereof, to form a second primer extension reaction admixture. The admixture is maintained under polynucleotide synthesizing conditions for a time period, which is typically predetermined, sufficient for the formation of a second primer extension reaction product.

In preferred strategies, the first and second primer extension reactions are the first and second primer extension reactions in a polymerase chain reaction (PCR).

PCR is carried out by simultaneously cycling, i.e., performing in one admixture, the above described first and second primer extension reactions, each cycle comprising polynucleotide synthesis followed by separation of the double-stranded polynucleotides formed.

PCR is preferably performed using a distinguishable variation of the standard protocol as described in U.S. Pat. Nos. 4,683,195 and 4,683,202 to Mullis et al., and No. 4,889,818 to Gelfand et al., and in the Innis & Gelfand reference described above, employing only one primer. The principles of the PCR process have been described under "Background of the Invention," supra. Typically, the DNA polymerase used in AP-PCR is the thermostable DNA polymerase purified from *Thermus aquaticus* and known as Taq I. However, other DNA polymerases can be used.

A PCR thermocycle is the changing of a PCR admixture from a first temperature to another temperature and then back to the first temperature. That is, it is cycling the temperature of the PCR admixture within (up and down through) a range of temperatures. Typically, the change in temperature is not linear with time, but contains periods of slow or no temperature change and periods of rapid temperature change, the former corresponding to, depending on the temperature, a hybridization (annealing), primer extension or denaturation phase, and the later to temperature transition phases. Thus, PCR amplification is performed by repeatedly subjecting the PCR admixture to a PCR temperature gradient where the gradient includes temperatures where the hybridization, primer extension and denaturation reactions occur. Preferred PCR temperature gradients are from about 35° C. to about 94° C., from about 40° C. to about 94° C., and from about 48° C. to about 94° C.

In one embodiment, at least one initial cycle of PCR is performed, starting with the arbitrary primer and the genomic nucleic acids to be amplified. Using Taq I polymerase, the initial cycle(s) of PCR are performed under "low stringency annealing (hybridization) conditions". The term "stringency" refers to the degree of mismatch tolerated during hybridization of the primer and template; the higher the stringency, the less mismatch is tolerated. Preferably, one to five cycles of amplification are performed under these conditions. These cycles are generally performed so as to have the following phases: 94° C. for 5 minutes to denature, 5 minutes at the low stringency annealing temperature, and 72° C. for 5 minutes for extension. More preferably, one to four or one to three low stringency amplification cycles are performed. Most preferred, are one or two low stringency amplification cycles. The low stringency annealing temperature can be from about 30° C. to about 55° C., preferably from about 35° C. to about 55° C., and more preferably from about 40° C. to about 48° C. If mixtures of primers that have considerable sequence degeneracy are used, higher temperatures for annealing in the initial cycle(s) can be tolerated, presumably because some of the sequences in the mixtures inevitably anneal quite well to any complex genome and efficiently generate amplification products.

Subsequently, in a second step, at least about 10, preferably about 10 to 40, cycles of PCR are performed under high stringency hybridization conditions. With Taq I polymerase, these cycles are generally performed so as to have the following phases: 94° C. for 1 minute for denaturation, the high stringency annealing temperature for 1 minute, and 72° C. for 2 minutes for extension. (See Example 2, infra.) Alternatively, other thermostable DNA polymerases can be used, in which case the denaturation, high stringency annealing, and extension temperatures are adjusted according to the thermostability of the particular DNA polymerase. The high stringency annealing temperature is about the melting temperature of the double-stranded DNA formed by annealing, about 35° C. to about 65° C., generally greater than about 55° C., and preferably about 60° C. Preferably, the annealing temperature in the second step is greater than the annealing temperature in the first step. The annealing temperature in the second step is lower for shorter primers, because the melting temperature of short double-stranded helices is decreased. Conversely, it is higher for longer primers.

Insofar as the objective in the present method is to produce a fingerprint composed of discrete DNA segments, it is to be understood that the low stringency hybridizatin conditions can be varied widely to allow the formation of arbitrarily primed primer extension reaction products. Because shorter primers have a higher number of sites on a genome for exact complementarity than longer primer, it is not required that the "low stringency hybridization conditions" be strictly maintained in the sense of stringency where the primer is short to yield the "arbitrarily primed reaction products". Rather, the objective is to produce a readable fingerprint, i.e., not having so many primer extension products as to be a smear, and not having so few products as to not yield a distinctive fingerprint.

Therefore, the hybridization conditions are selected, in the context of the primer length, as to be compatible with arbitrarily priming the target nucleic acid, where the objective is to produce a discrete set of DNA fragments using an arbitrary primer according to the present invention. Thus, if the primer selected is long, it is necessary that the hybridization conditions be of lower stringency, favoring more mismatches, whereas, if the primer is short, the hybridization conditions can be of relatively higher stringency, in order to generate the first set of discrete DNA segments. Thereafter, a second round of PCR amplification is conducted to increase the amount of discrete DNA segments formed up to a detectable level. This second round of PCR amplification is typically conducted under high stringency conditions, where there is high hybridization specificity and no mismatches.

The reaction is performed in a buffer optimized for activity of the particular thermostable DNA polymerase employed. A number of thermostable DNA polymerases have been isolated. See U.S. Pat. No. 4,889,818 describing the thermostable DNA polymerase of *Thermus aquaticus*. In addition, the thermostable DNA polymerases present in any of the thermophillic bacteria is well known and described in U.S. Pat. No. 4,889,818.

The particular AP-PCR conditions employed will depend at least upon the particular thermostable DNA polymerase used for the amplification reaction and are typically optimized for that particular thermostable DNA polymerase. Effective amounts of the primer(s) and target nucleic acid are admixed in an aqueous PCR buffer that includes an effective amount of an inducing agent, an effective amount of each dNTP. For Taq DNA polymerase, the buffer typically contains an effective amount of Taq, 50 mM KCl, 10 mM Tris-HCl, pH 8.4, 4 mM $MgCl_2$, and 100 µg/ml gelatin. Each deoxyribonucleoside triphosphate (i.e., A, T, G and C) is typically present at about 0.2 mM concentration when Taq DNA polymerase is used.

The extent to which any particular sequence can be amplified by AP-PCR depends on three general factors: (1) the frequency of priming at flanking sites; (2) the ability of the DNA polymerase used, typically Taq polymerase from *Thermus aquaticus*, to extend the template completely; and (3) the total number of productive cycles.

E. Comparison of the DNA Amplification Products with those Produced from known Genomes If the object of the performance of the AP-PCR method is to identify the genome from which the discrete products were produced, the DNA amplification products obtained from a sample are compared with the amplification products resulting from the performance of AP-PCR on nucleic acids isolated from known genera, species, subspecies and/or strains using the same primer or mixture of primers, in separate reactions.

The samples selected for comparison depend on the expected identification of the test organism of unknown genome. In many clinical situations, identification of an organism of an unknown bacterial genome can be narrowed down by means of the site of infection or other clinical factors. For example, the presence of a wound infection may suggest that the test organism is a member of the genus Staphylococcus. If the unknown organism might be Staphylococcus, various species of Staphylococcus, such as *S. haemolyticus, S. hominis, S. aureus, S. warneri* and *S. cohnii*, are used; multiple strains can be used for each species. Similarly, if the unknown organism might be a strain of Streptococcus, the samples selected for comparison are various identified strains of Streptococcus. If the unknown organism is a bacterium of enteric origin, various strains of Escherichia, Klebsiella, Enterobacter, Serratia, Salmonella, Shigella, Proteus and Providencia are used.

Because the most substantial differences in the AP-PCR amplification products from different bacterial isolates represent differences between species, AP-PCR can be used effectively to reveal a prior misassignment of a strain. Strains that have been assigned to the wrong species are very rapidly uncovered by the AP-PCR method. Typically, when AP-PCR is used to verify the assignment of a bacterial isolate to a species, the primer is chosen to maximize interspecific difference of the discrete DNA amplification products generated by AP-PCR. Primers for this application typically exclude regions substantially complementary to regions of DNA highly conserved between the species being studied.

The comparison between the AP-PCR products of the organism of unknown genome and those produced from known genomes is typically performed by separating the discrete DNA amplification products in an apparatus containing a medium capable of separating DNA fragments by size in order to produce a "fingerprint" of the amplification products as separated bands, and then comparing the fingerprint patterns. The fingerprint patterns are diagnostic of the genus, species, and/or strain to which the test organism of unknown genome belongs. Generally, such separation is carried out by electrophoresis, for example, using gel electrophoresis on agarose or polyacrylamide gels to display the resulting DNA products for visual examination. Many protocols for electrophoresis are known in the art; see U.S. Pat. No. 4,729,947 and B. Perbal, "A Practical Guide to Molecular Cloning," Ch. 9, "Separation of DNA Fragments by Electrophoresis," pp. 340–362, 2d ed., John Wiley & Sons, New York (1988), incorporated herein by this reference.

One such representative technique is electrophoresis through 5% polyacrylamide containing 50% urea. The concentration of acrylamide is varied according to the size of the products to be resolved. Commercially available size markers typically derived from the digestion of a plasmid or phage of known sequence with a restriction enzyme are added to the gel.

The individual bands present in the fingerprint are detected by various techniques, such as ethidium bromide staining. At least one of the deoxyribonucleotide triphosphate monomers used in the second stage of the reaction can be radioactive, allowing detection of the bands of the fingerprint by autoradiography, or the primer itself can be radioactively labeled by treatment with an appropriate kinase. Alternatively, fluorescent nucleotides can be incorporated and detection carried out by means of fluorescence.

F. Further Manipulation of Fragments Produced by AP-PCR

Isolated separated fragments can be cleaved with a restriction endonuclease capable of generating polymorphisms, such as TaqI or MspI. Separated fragments produced by AP-PCR and resolved on gels can also be isolated from the gel and reamplified in a conventional PCR procedure to increase the quantity of the isolated band. Isolated fragments can, if desired, be cloned in a bacterial host, typically a strain of *Escherichia coli*, capable of preserving the integrity of any genetically unstable DNA structures such as long, direct and inverted repeats. Such cloned bands then can be sequenced by well-known, conventional techniques, such as the Sanger dideoxynucleotide sequencing technique or the Maxam-Gilbert chemical cleavage sequencing technique.

For many procedures, such as the preparation of DNA probes, it is not necessary either to clone or recut the DNA fragments amplified by AP-PCR and isolated from the gel. Such fragments can be used as probes after further amplification by conventional PCR during which radioactive nucleotides are incorporated in the amplified fragments.

II. Application to Identification of Staphylococcus Species

One significant application of the general method of the present invention is the identification of the species to which an isolate of Staphylococcus belongs. Staphylococcus is a human pathogen and frequently responsible for serious infections occurring in surgical patients. Accordingly, rapid identification of Staphylococcus species is particularly important in a clinical setting.

In the identification of Staphylococcus species by AP-PCR, the discrete DNA amplification products produced from the sample of DNA from the test organism are compared with the DNA amplification products produced from known Staphylococcus species when the same primer is used. We have found between three and twenty products predominate in the AP-PCR products obtained from Staphylococcus genomes. These products are species-specific and can be used to distinguish between *S. haemolyticus, S. hominis, S. aureus, S. warneri* and *S. cohnii*. In some cases, subspecies and/or strains of these species are also distinguished. (See Example 6, infra).

III. Application to Identification of Streptococcus Strains

In a similar manner, AP-PCR can be used to identify particular strains of Streptococcus. In the identification of Streptococcus strains by AP-PCR, the discrete DNA amplification products produced from the test organism of unknown strain are compared with the DNA amplification products produced from DNA of known Streptococcus strains when the same primer is used. Streptococcus is also an important human pathogen, causing potentially severe infections of the skin and mucous membranes, and its rapid identification is clinically important.

As shown below in Example 7, AP-PCR performed on a number of strains of Streptococcus reveals a fingerprint of amplified bands with some species-specific features, as well as some isolate-specific differences. One can clearly group almost all members of a species based on common bands and group subsets of strains within species based on shared bands that are not present in other strains.

IV. Application of AP-PCR to Genetics of Eukaryotes

The DNA sequences that represent polymorphisms differing from individual to individual of a species obtained from application of the AP-PCR method of the invention are useful in genetic mapping of eukaryotes, including plants such as maize and soybeans, animals, and humans. In particular, AP-PCR can be used to reveal polymorphisms based on the AP-PCR fingerprint. Such polymorphisms are particularly useful for genetic mapping. The polymorphisms generated can be correlated with other markers such as restriction fragment length polymorphisms (RFLPs), which in turn have been linked to genetic markers of known function. A RFLP is a detectable difference in the cleavage pattern of DNA from different individuals of a particular species when that DNA is cleaved with a particular restriction endonuclease. Such differences arise when a mutation affects the sequence cut by the enzyme, removing a site previously present or adding a new site.

AP-PCR can be used to track genetic differences in rice, with a 600-megabase haploid genome (Example 8) and in maize, with a 3000-megabase haploid genome (Example 9). Maize has a genomic complexity comparable to that of the human genome. Similar results are expected with soybeans.

The heterozygosity of the maize genome has been estimated to be about 0.05. Each primer used in the AP-PCR method can probably detect more than one polymorphism between strains at that level of heterozygosity.

Such approaches should allow determination of the linkage distance between polymorphisms and various phenotypes. Phenotypes can be scored in a number of ways, including morphological features and molecular features, such as electrophoretic mobility on proteins and variations in intensity of proteins on two-dimensional gels (Higginbotham et al., "The Genetic Characterization of Inbred Lines of Maize (*Zea mays* L.) Using Two Dimensional Protein Profiles," Symposium, 1990). It is interesting to note that when protein abundance or state of modification is followed as a phenotype, linkage is to the genetic element that causes that variation and often not to the protein being observed. Such genetic element can be a regulator or other control element, or a gene for a modifying enzyme. It is possible, however, to link many protein electrophoretic mobility variants to the AP-PCR map.

A polymorphism can be correlated with a phenotypic character through repeated backcrossing. This introgression method simplifies the background. Comparing the backcrosses with the parents detects polymorphisms linked to the gene of interest.

Another application of the AP-PCR method is in creating a physical AP-PCR map by correlating the recombination frequencies between AP-PCR fragments. By choosing the crosses used in the development of the physical map judiciously, the AP-PCR map will automatically orient itself with respect to the genetic map. Such physical linkage can be studied by pulsed field electrophoresis (PFE). By applying restriction endonucleases making rare cuts, PFE, and Southern blotting to maize or soybean DNA and probing with genetically linked AP-PCR probes, the size of the physical region for large fragments of chromosomes isolated by PFE can be compared with the rate of recombination. Analogous techniques can be employed for mapping the mouse or human genome. This is of interest because recombination is not equal throughout the genome. The AP-PCR method is particularly suitable for this purpose because a great many markers can, in principle, be identified for an area of interest.

The number of individual progeny from crosses that can be inspected and the amount of polymorphism in each marker determines the accuracy with which markers can be mapped. The segregation of polymorphisms revealed by the AP-PCR method in the context of the RFLPs that are already mapped improves the ability to measure genetic distance between them. Computer programs are available for genetic linkage analysis including LIPED (Ott, *Amer. J. Human Genet.* 28:528–529 (1976) for two point linkage analysis, ILINK and CILINK from the LINKAGE package (Lathrop et al., *Proc. Natl. Acad. Sci. USA,* 81:3443–3446, 1984; Lathrop et al., *Amer. J. Human Genet.,* 37:482–498, 1985), GMS (Lathrop et al., *Genomics,* 2:157–164, 1988), and MAPMAKER (Lander et al., *Genomics,* 1:174–181, 1987) for multipoint analysis. Additionally, quantitation of the bands allows distinction between homozygotes and heterozygotes for a particular band in the AP-PCR fingerprint.

The use of such linkage analysis techniques allows determination of linkage distance between the polymorphisms and various phenotypes. RFLPs that have been linked to interesting genetic markers can be correlated with the AP-PCR map. For example, tightly linked flanking RFLP markers have been found for the Mdml gene on chromosome 6S in maize. This gene is involved in resistance to Maize Dwarf Mosaic Virus (MDMV) (McMullen et al., *Mol. Plant-Microbe Interactions,* 2:309, 1989). Similarly, a RFLP marker less than 1 centiMorgan (cM) from the Htl1 gene, which confers resistance to the fungal pathogen *Helminthosporum turcicum,* has been found (Bentolila et al., Symposium, 1990).

Another approach to mapping makes use of the fact that RFLPs themselves can be generated from AP-PCR fingerprints. For instance, TaqI restriction endonuclease, which recognizes the site TCGA, will cleave AP-PCR products in which there is at least one TaqI site. If a TaqI site is present in one of the AP-PCR fingerprint products in some individuals but not in others, there will be a difference in the fingerprint of TaqI digested DNA from these individuals. This allows the detection of TaqI RFLPs from AP-PCR patterns. Such TaqI RFLPs are among the most common RFLPs known in the genome because the TaqI recognition site contains the hypermutable dinucleotide CpG. Similarly, MspI digests, cut at the recognition site of CCGG, can be used to detect the relatively abundant MspI polymorphisms. Such RFLPs can be either mapped directly in families by genetic mapping or cut out of gels and amplified with radioactively labeled deoxyribonucleoside triphosphates, such as α-labeled triphosphates, in conventional PCR to use them to probe Southern blots of the appropriately cleaved human DNAs. To ensure purity, the extracted fragments can be recut with the same enzyme following extraction. Alternatively, the bands isolated from AP-PCR fingerprints can be cloned and sequenced. Preferably, such bands should be cloned in Sure *E. coli* (Stratagene Cloning Systems, San Diego, Calif.) to preserve the integrity of terminal repeats.

One type of polymorphism that is expected to be revealed by the AP-PCR method is the variable number tandem repeats (VNTRs). VNTRs have been shown to be associated with highly repetitive regions in the genome, including minisatellite repeats such as the dispersed simple repeat $(GT:CA)_n$ (Litt et al., *Am. J. Hum. Genet.*, 44:397–401, 1989) and VNTR repeats of 9 to 40 bases (Jeffreys et al., supra). The dispersed simple repeat $(GT:CA)_n$ should be primed by primers with TGTGTG at the 3'-end. The repeats of 9 to 40 bases may have the sequences GGGCAGGAXG (SEQ ID NO:15) or GXXXXTGGG (SEQ ID NO:16). Primers containing these sequences at the 3'-end should prime these repeats of 9 to 40 bases. These primers are "arbitrary" in the sense that the location of the particular repetitive sequence in the genome need not be known, nor must the primer have a perfect match with any particular occurrences of the repeat in the genome.

Yet another source for the generation of polymorphisms by the AP-PCR method is associated with the sequence CpG. This dinucleotide is more polymorphic than other dinucleotides in certain animal and plant genomes, because it is a target for methylation. Primers with CpG located near the 3'-end are expected to be effective in generating polymorphisms because of this variability. In particular, a primer with a sequence of ACGCGAC at the 3'-end that combines a RY repeat, similar to the GT repeat, with two CG dinucleotides, is expected to be an effective generator of polymorphisms when used as a primer in AP-PCR. Similarly, primers with alternating purine and pyrimidine residues near their 3'-ends are also expected to be effective in generating polymorphisms.

These techniques can also be employed to analyze animal genomes, including the genomes of mice, as well as the human genome. They are particularly useful for filling in the genetic map by linking known markers more precisely. An example of the detection by AP-PCR of polymorphisms resulting from the crossing of inbred mouse strains is shown in Example 11.

The AP-PCR method of the invention permits genetic mapping of DNA polymorphisms in mammals without having to first identify RFLP probes. Each polymorphic band in the fingerprint produced by the method represents a heritable characteristic. No clones must be made or plasmids purified. Polymorphisms can be generated by almost any primer selected. The technique requires less than 1/100 of the amount of genomic DNA per lane compared to that needed to prepare a Southern blot for conventional RFLP analysis. The method can use ethidium detection, fluorescent detection or only small amounts of labeled bases relative to Southern hybridization. Moreover, AP-PCR generated DNA polymorphisms can be isolated directly from gels and reamplified to use as probes in "genome walking" or restriction mapping strategies without cloning. Sequencing of some of these polymorphisms will also not require cloning.

One approach for using the AP-PCR method in human genetics can produce products assignable to the human fragment in a somatic cell hybrid. As long as the recipient is the same for a set of hybrids, the products that will be different from a non-hybrid control AP-PCR will be the human fragments. Such bands would assign the human fragment on the genetic map if the band was already genetically assigned. Also, such bands can be isolated from the gel and used to make a DNA probe. An example of the AP-PCR method using somatic cell hybrids is shown in Example 10.

EXAMPLES

In order that the invention described herein may be more fully understood, the following examples are set forth. It should be understood that the following examples are for illustrative purposes only and are not to be construed as limiting the invention.

1. Isolation of DNA for AP-PCR

Strains of Staphylococcus listed in Table 1 were grown overnight at 37° C. in 2–5 ml of brain heart infusion media. The cells were pelleted, resuspended in 0.2 ml of TE (0.01 M Tris-HCl, pH 8.0, 1 mM EDTA) with 0.2 mg/ml lysostaphin and incubated at 37° C. for one hour. Following this incubation, 0.2 ml proteinase K solution (containing 0.5 mg/ml proteinase K, 1% Sarkosyl, 200 mM EDTA, and 1 mM calcium chloride) was added to each sample. The samples were then digested at 50° C. for one hour. The clear lysates were extracted with phenol and then chloroform; the DNA was then precipitated with ethanol. The precipitated DNA was dissolved in TE, and its final concentration was estimated by agarose gel electrophoresis and ethidium bromide staining.

TABLE 1

STAPHYLOCOCCUS STRAINS

| Species | Strain Designation | Origin |
| --- | --- | --- |
| S. haemolyticus | AW 263 | Human |
| | ATCC 29970 | Human |
| | PAY 9F2 | Chimpanzee |
| | MID 563 | Mouse lemur |
| | CC 12J2 | Mangabey |
| S. hominis | ATCC 27844 | Human |
| | ATCC 27846 | Human |
| S. aureus | ISP 8 | Human |
| | ATCC 8432 | Bird |
| | ATCC 15564 | Human |
| | ATCC 6538 | Human |
| | Sau 3A | Human |
| | ATCC 12600 | Human |
| S. warneri | GAD 473H | Bush-baby |
| | MCY 3E6 | Rhesus monkey |
| | CPB 10E2 | Cercopithecus |
| | LED 355 | Lemur |
| | PBNZP 4D3 | Langur |
| S. cohnii | JL 143 | Human |
| | LED 3104 | Lemur |
| | CM 89 | Human |
| | SS 521 | Squirrel monkey |

Strains designated as ATCC are deposited with the American Type Culture Collection. Other abbreviations are arbitrary designations for laboratory strains.

2. Performance of AP-PCR Amplification

Reactions, with a volume of 10 μL, were prepared containing 1×Taq polymerase buffer (Stratagene Cloning Systems, San Diego) adjusted to 4 mM with $MgCl_2$, 0.2 mM of each deoxyribonucleotide triphosphate, 10 μM Kpn-R primer, and DNA at various quantities from 7.5 ng to 0.12 pg as indicated. The reactions were overlaid with oil and cycled through the following temperature profile: 94° C. for five minutes for denaturation, 40° C. for five minutes for low stringency annealing and 72° C. for five minutes for extension. This temperature profile was followed for two cycles. Then 10 high stringency cycles were performed with the following temperature profile: 94° C. at one minute, 60° C. for one minute, and 72° C. for ten minutes. At this point, 90 µL of a solution containing 1×Taq polymerase buffer, 0.2 mM of each deoxyribonucleoside triphosphate, and 50 µCi α-[$^{32}$P] dCTP was added and 30 additional high stringency cycles were performed. This protocol was designed to provide high primer concentration during the low stringency steps to maximize the priming efficiency during the initial cycles of PCR, before the sequences had been greatly amplified.

3. Effect of Variation of Temperature for Low Stringency Annealing in AP-PCR

AP-PCR was performed as in Example 2, above, using 1 ng of DNA from *S. aureus* ISP 8 DNA, except that the temperature for low stringency annealing in the first two PCR cycles was varied. The results are shown in FIG. 1. Lane 1 of FIG. 1 was performed at 60° C., typical for conventional PCR; Lane 2, 36° C.; Lane 3, 40° C.; Lane 4, 44° C.; Lane 5, 48° C.; and Lane 6, 52° C. Lane M is Hind III-digested bacteriophage DNA.

As shown in FIG. 1, the pattern of bands changes only slightly as the temperature is raised, until, at some point, the temperature is too high for efficient annealing by the arbitrarily chosen primer. These results indicate that AP-PCR can use a relatively broad range of temperatures for low stringency annealing.

4. Effect of Variation of Template DNA Concentration in AP-PCR

AP-PCR was performed as in Example 2, above, using DNA from *S. aureus* strain ISP 8, except that the concentration of DNA used as template was varied. Each series of five different concentrations was from three independent dilutions.

Template concentrations used were 7500 pg, 1900 pg, 470 pg, 120 pg, 30 pg, 7.5 pg, 1.9 pg, 0.48 pg and 0.12 pg. The pattern generated by AP-PCR using a 34-base primer (Kpn-R) is very consistent for template concentrations between 7.5 ng and 10 pg. Below 10 pg the production of discrete fragments is more sporadic, but the products produced are almost all represented at higher concentrations. For a genome of 3×10$^6$ bp, 10 pg of template DNA is equivalent to 3000 complete molecules.

One interpretation of this data is that even the best priming events are quite inefficient and at this low template concentration each AP-PCR event has about a 1 in 55 (square root of 3000) probability of initiating during each of the two low temperature cycles. Thus, at a template concentration of 3000 molecules of DNA, each possible AP-PCR event is likely to initiate. However, at lower template concentrations, such calculations suggest that some potential initiations are missed, so that, for maximum coverage of the genome, it is desirable to use at least a quantity of DNA corresponding to 3000 complete Staphylococcus genomes.

5. Intra-Specific Pattern of AP-PCR Products from *S. Aureus*

We compared the pattern of AP-PCR products from six *S. aureus* strains, using varying quantities of template DNA. The strains were fingerprinted by AP-PCR using the standard protocol of Example 2 except that five different quantities of template were used: 7.5 ng, 1.9 ng, 470 pg, 120 pg and 30 pg of DNA per reaction. The strains used were strains ISP-8 (A), ATCC 8432 (B), ATCC 15564 (C), ATCC 6538 (D), Sau 3A (E), and ATCC 12600 (F). The resulting amplified material was resolved by electrophoresis through a 5% polyacrylamide gel containing 50% urea.

Figure 2:
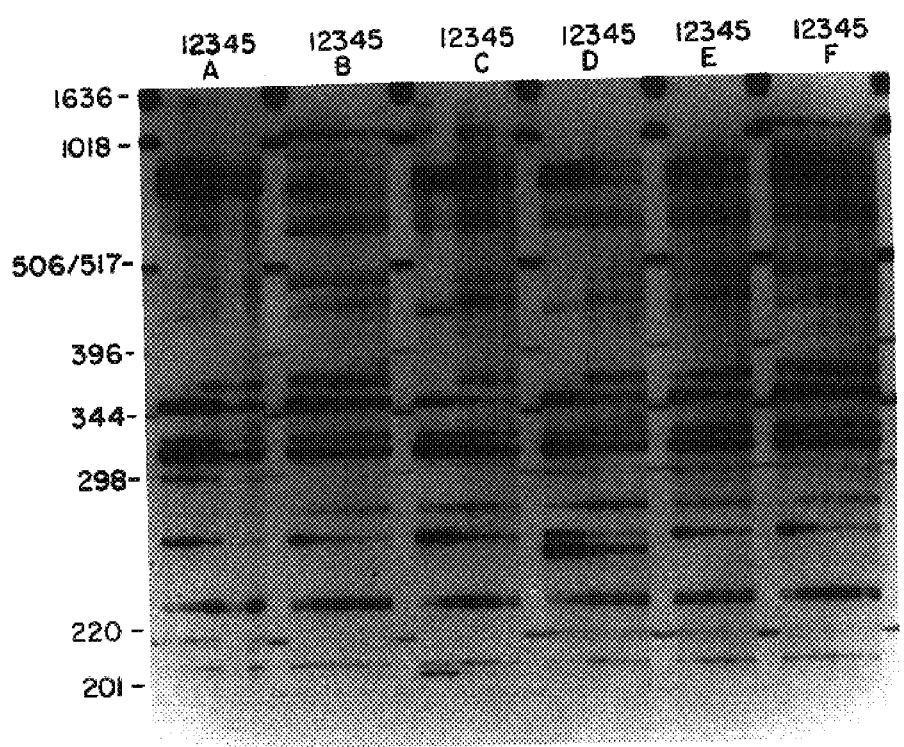
FIG. 2 shows the AP-PCR patterns produced by six strains of *S. aureus* at five different concentrations of DNA, as described in Example 5, infra.

The results are shown in FIG. 2. Size markers shown in FIG. 2 are the 1 Kb ladder from BRL/Gibco (Gaithersburg, Md.). Over this range of DNA concentration, the patterns are highly reproducible and also very similar between strains. The differences between strains is diagnostic of similar strains in their relationships. Primers of similar size but different sequence gave a different pattern, but similar intra-specific variations. These results show that AP-PCR can identify and categorize bacterial strains.

6. Species-Specific AP-PCR Products from Staphylococcus Species

Fingerprints of 17 isolates representing four different species of Staphylococcus were obtained by AP-PCR. The protocol of Example 2 was used with 16 ng of template DNA per reaction. The species and strains fingerprinted were: (1) *S. haemolyticus*, strains CC 12J2 (lane 1), PAY 9F2 (lane 2), AW 263 (lane 3), MID 563 (lane 4), and ATCC 29970 (lane 5); (2) *S. warneri*, strains CPB 10E2 (lane 6), GAD 473 (lane 7), MCY 3E6 (lane 8), PBNZP 4D3 (lane 9), and LED 355 (lane 10); (3) *S. hominis*, strains ATCC 27844 (lane 11), ATCC 27846 (lane 12), and Ful (lane 13); (4) *S. cohnii*, strains JL 143 (lane 14), CM 89 (lane 15), and SS 521 (lane 16); and (5) *S. aureus*, strains ISP-8 (lane 17), ATCC 8432 (lane 18), ATCC 15564 (lane 19), ATCC 6538 (lane 20), Sau 3A (lane 21), and ATCC 12600 (lane 22). (The lane designations refer to the gel shown in FIG. 3.) The resulting amplified material was resolved by electrophoresis through 5% polyacrylamide containing 50% urea; size markers were as in Examples 4 and 5.

Figure 3:
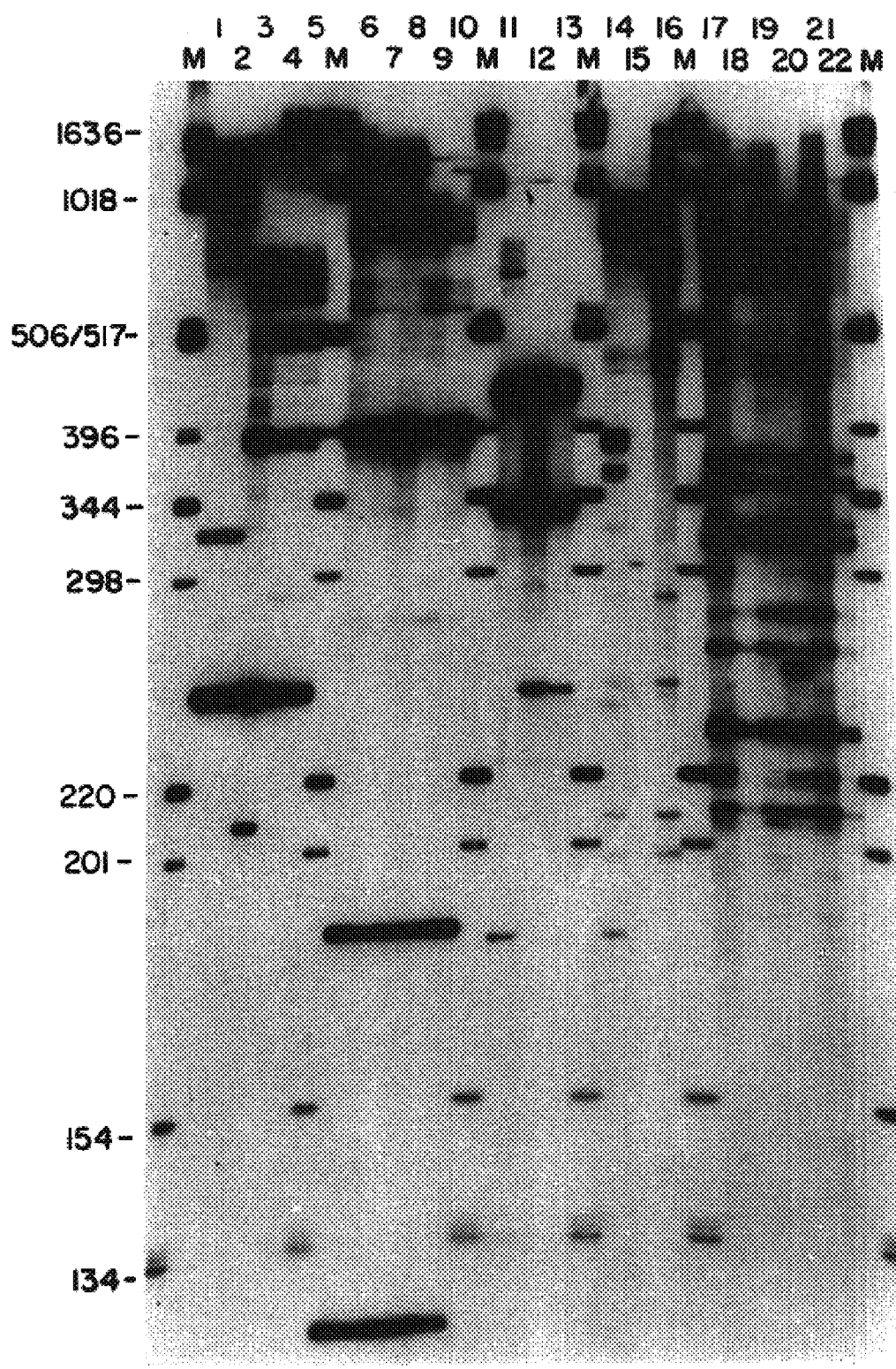
FIG. 3 shows the AP-PCR patterns produced by 17 isolates representing four different species of Staphylococcus, illustrating the differences apparent between species, as described in Example 6, infra.

The results are shown in FIG. 3. In general, there is a species-specific pattern of AP-PCR products, observed, for example, in amplification of DNA from *S. warneri* two distinct patterns. These patterns share only one AP-PCR product but have at least three prominent products that are not shared. The differences in products were dramatic and are presumably the result of a considerable difference in DNA sequence between these strains. The most likely possibility is that *S. haemolyticus* has two distinct "subspecies." It is interesting to note that one "subspecies" AP-PCR pattern is produced by *haemolytigus* strains AW 263, ATCC 29970, and PAY 9F2, strains that live on higher primates such as humans and chimpanzees, while the other strains of *haemolyticus* with the other AP-PCR pattern, MID 563 and CC 12J2, are from lower primates such as mangabey and lemur. Similarly, the three *S. cohnii* strains were quite divergent, but recognizably related.

The AP-PCR products are species or subspecies specific and are not preserved even between relatively closely related species, such as the *haemolyticus-warneri-hominis* group. A few AP-PCR products may be shared between species. For instance, the product of about 400 base pairs in *S. warneri* may be the same as a product seen in the *haemolyticus* strains PAY 9F2, AW 263, and ATCC 29970, although coincident migration of fragments of different sequence might explain these results.

7. Strain-Specific AP-PCR Products from Streptococcus Strains

Twelve strains of Streptococcus were fingerprinted by AP-PCR with the standard protocol, as used in Example 6, with M13 reverse sequencing primer as the arbitrarily chosen primer and two different amounts of template: 18.8 and 4.7 ng per reaction. The resulting amplified material was resolved by electrophoresis through 5% polyacrylamide gels containing 50% urea. Size markers were the same as those used in Examples 4–6.

Figure 4:
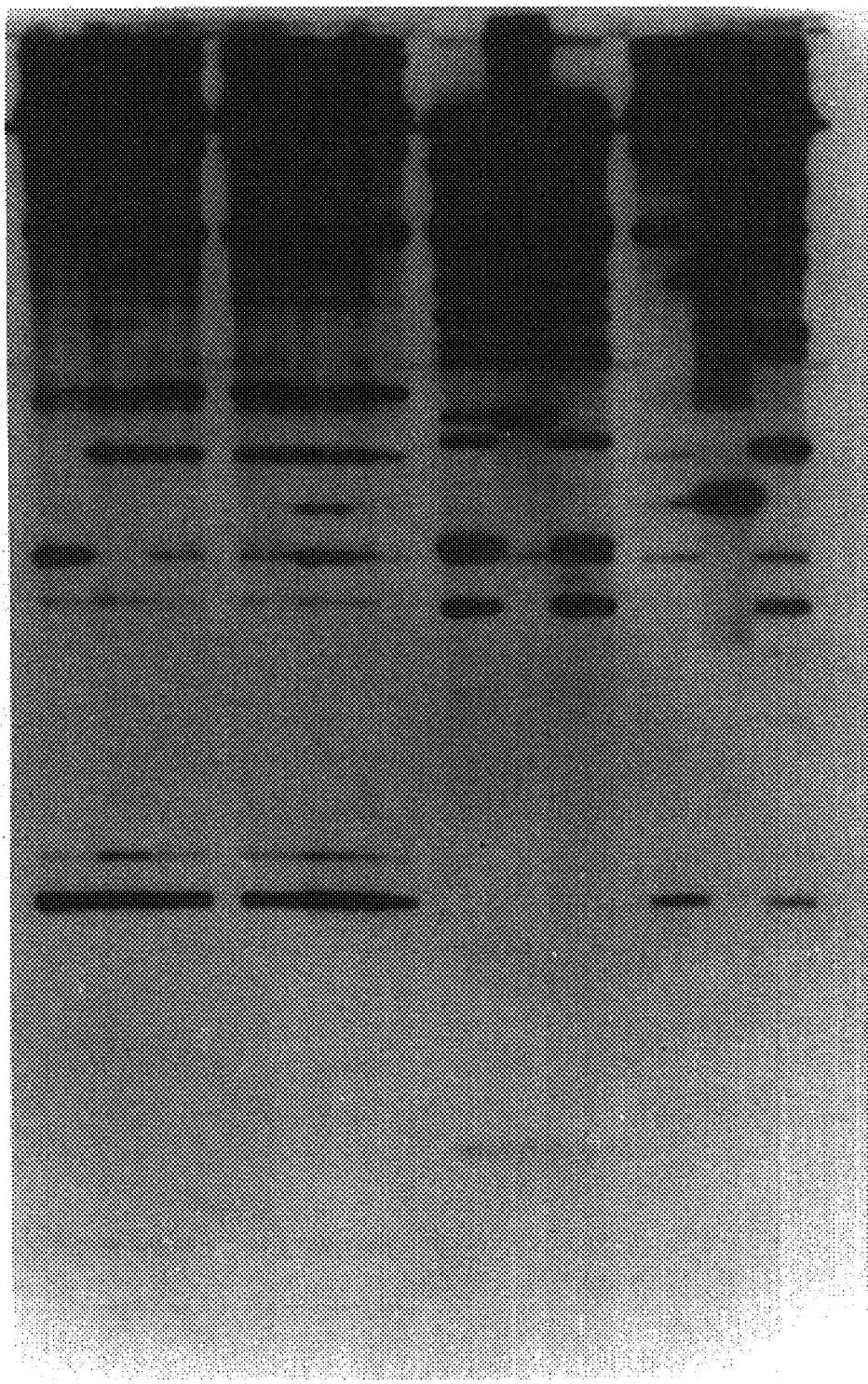
FIG. 4 shows the AP-PCR patterns produced by six strains of Streptococcus, illustrating the differences detectable between the strains and the general similarity of the patterns from the same species, as described in Example 7, infra.

The results are shown in FIG. 4. The strains shown are as follows: Group 1, D471; Group 2, TI/195/2; Group 3, 40 RS 1; Group 4, 2 RS 15; Group 5, 47 RS 15; Group 6, 55 RS 15; Group 7, 1/E9; Group 8, T28/51/4; Group 9, K58 Hg; Group 10; SM6; Group 11, OGI X; and Group 12, UAB 092. Each group consists of two lanes in the gel; in the first lane, 18.8 ng of DNA was used, while in the second lane, 4.7 ng of DNA was used.

Figure 5:
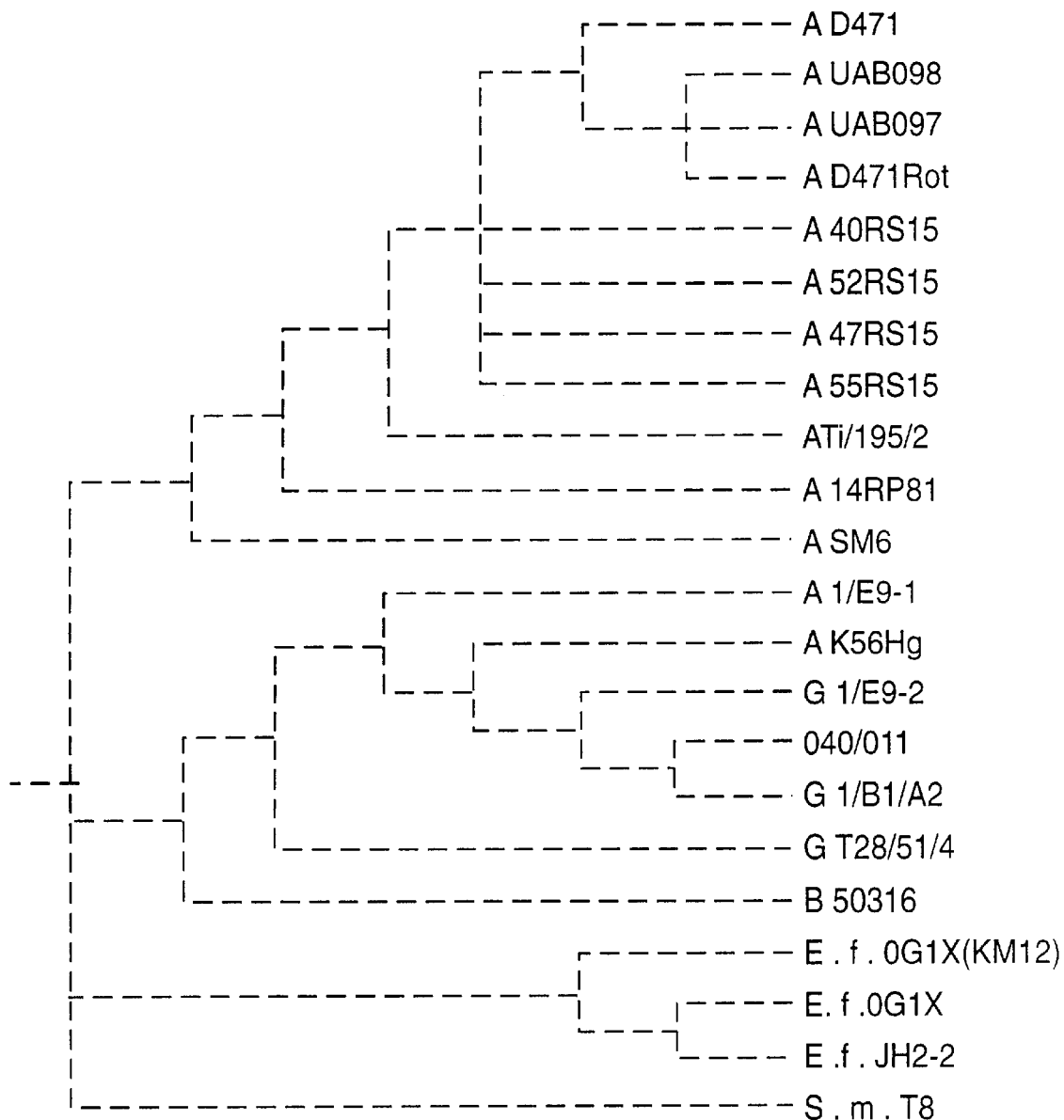
FIG. 5 shows a dendrogram indicating the relative genetic distance between the strains on which the AP-PCR method was performed on Example 7, infra.

The results show that subsets of strains within species can be grouped, based on shared bands. Further work with AP-PCR on Streptococcus, with the M13 reverse sequencing primer and a second primer, Kpn-R, resulted in a dendrogram developed by a distance matrix method to show the relationships of the strains. This dendrogram, which depicts the relative genetic distance of the Streptococcus strains tested, is shown as FIG. 5.

8. Strain-Specific AP-PCR Products from Inbred Rice Strains

Three independent inbred strains of rice, designated G1, G2, and G3, were fingerprinted using the standard AP-PCR protocol as used in Examples 5, 6, and 7, with M13 reverse sequencing primer, at four concentrations of template DNA: 51 ng, 12 ng, 3 ng, and 0.8 ng per reaction.

Figure 6:
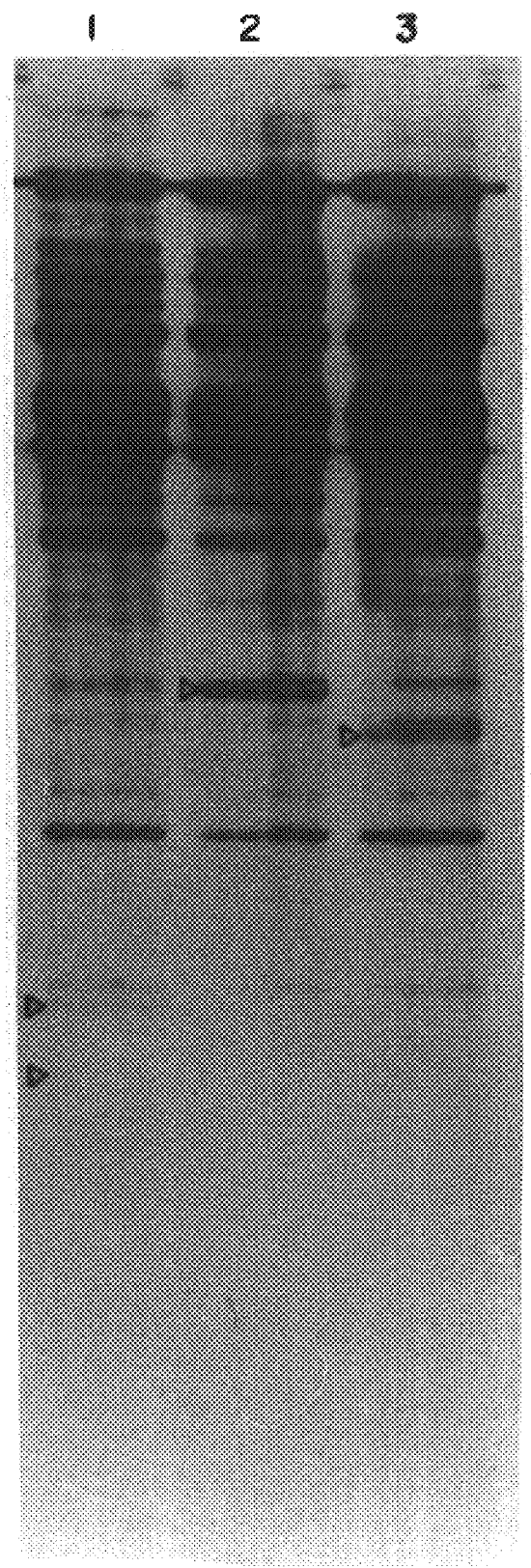
FIG. 6 shows the AP-PCR patterns produced by three strains of inbred rice, illustrating the existence of polymorphisms, as described in Example 8, infra.

The results are shown in FIG. 6. The three strains, G1, G2, and G3, are shown left to right on the gel. These three strains can be distinguished from each other. In particular, several polymorphisms (bands that differ from one strain to another) are visible. These polymorphisms are marked with arrows in FIG. 6.

These results demonstrate that plant varieties can be identified and categorized by the AP-PCR method.

9. Strain-Specific AP-PCR Products from Inbred Maize Strains and Their F1 Progeny AP-PCR fragments were obtained from several inbred strains of maize and from the F1 progeny of these strains. DNA from these strains was subjected to AP-PCR using the standard protocol, as used in Examples 5, 6, and 7, with three different quantities of template DNA: 64 ng, 16 ng, and 4 ng per reaction, using the modified M13 reverse sequencing primer with an extra G residue at its 3'-end.

On the gel, Groups 1–6 represent individual inbred strains, while Groups 7–9 represent the F1 generation from crosses of such individual inbred strains. The individual strains are as follows: Group 1, B73; Group 2, Mo17; Group 3, DE811; Group 4, Oh43; Group 5, FR16; Group 6, H99. The crosses are as follows:. Group 7, B73×Mo17; Group 8, B73×De811; Group 9, B73×Oh43. The parents of the progeny from crosses can be ascertained by comparison of the polymorphisms indicated by dots. These results show that AP-PCR can distinguish strains of maize and that the patterns are heritable.

10. Specific AP-PCR Products from Human DNA and Somatic Cell Hybrids

AP-PCR was performed on human DNA and DNA from somatic cell hybrids between human cells and mouse or Chinese hamster cells. AP-PCR was performed according to the standard protocol with a 20-base primer. In some cases, as shown in FIG. 7, 127, 32, and 8 ng of DNA were used per reaction; in other cases, only 32 ng of DNA was used.

Figure 7:
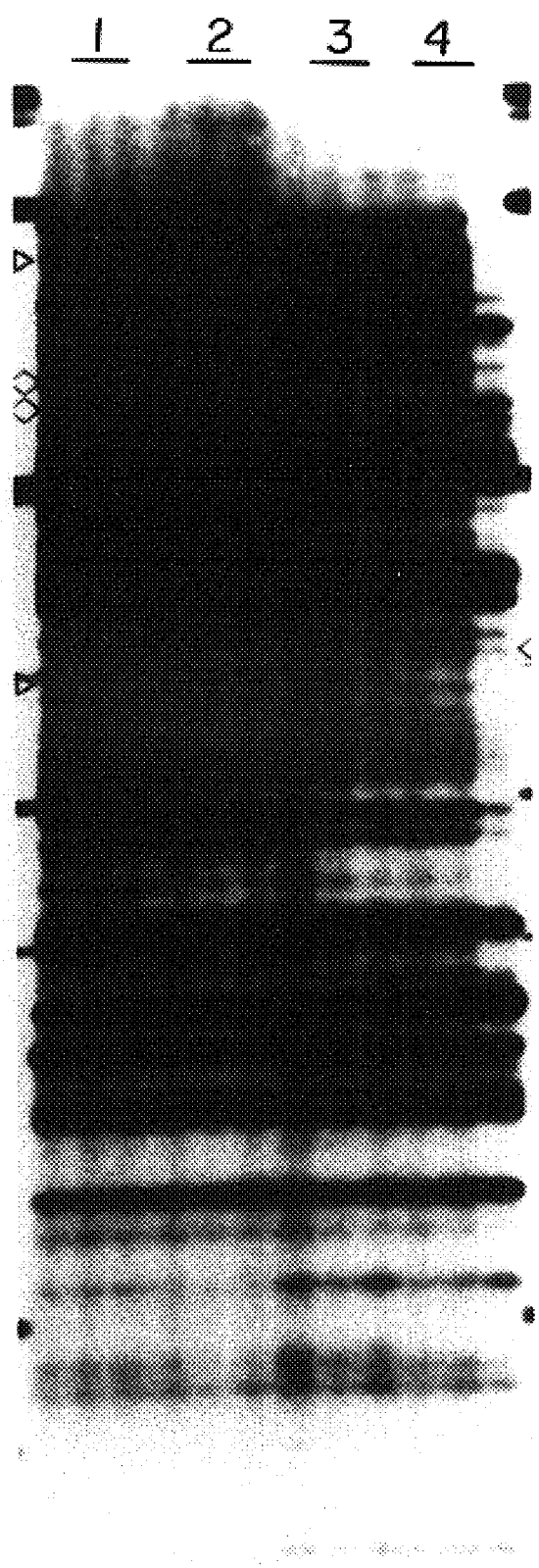
FIG. 7 shows the AP-PCR patterns produced by several samples of human DNA from individuals of different race and sex at three different concentrations, showing several polymorphisms and possible sex differences, as described in Example 10, infra.

The results are shown in FIG. 7. FIG. 7 shows the results when human DNA from: Group 1, Black female; Group 2, Caucasian female; Group 3; Black male; and Group 4; Caucasian male was used at three different DNA concentrations. Several polymorphisms are indicated; also indicated are possible sex-linked differences.

These data show that some AP-PCR products will be from the human genome and that these products can be mapped to a particular human chromosome.

11. Detection of Polymorphisms by AP-PCR in Inbred Strains of Mice

AP-PCR can be used to detect polymorphisms in mouse inbred lines. Most primers gave at least one polymorphism between most strains. Recombinant inbred lines of C57BL/6J×DBA/2J were obtained from Jackson Laboratories. AP-PCR was performed on genomic DNA from the parental strains, the F1 generation, and 26 recombinant inbred strains, using the standard protocol of Example 3 above, with the primer Kpn-R and 40° C. initial low stringency steps. The resulting products were resolved by electrophoresis in 1×TBE (0.09 M Tris-borate, 0.002 M EDTA) through a 5% polyacrylamide gel containing 50% urea.

Figure 8:
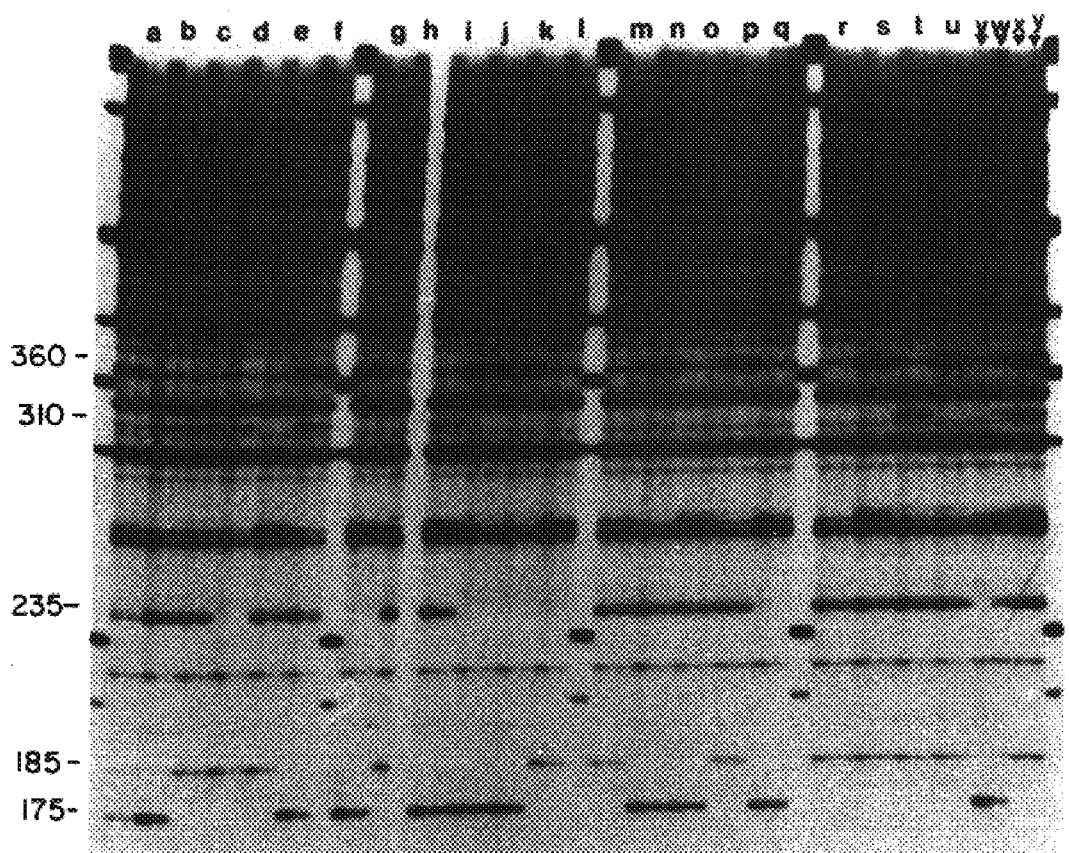
FIG. 8 shows the AP-PCR patterns produced by several samples of DNA from inbred mouse lines, including the lines C57BL/6J and DBA/2J, the F1 generation resulting from a cross between those lines, and 21 recombinant inbred lines, revealing several mappable polymorphisms, as described in Example 11, infra.

The results are shown in FIG. 8. Each lane consists of two concentrations of template, 50 ng on the right and 25 ng on the left. Lanes V and X are the two parental strains C57BL/6J and DBA/2J; lanes A and W are the F1 generation; and lanes B to U and Y are 21 recombinant inbred strains. Polymorphisms were seen at 360, 310, 235, 185, 175, and 115 bases. The polymorphisms at 185 and 175 bases were mutually exclusive and, thus, a length polymorphism. Four of these polymorphisms were mappable; three scored as the presence or absence of a band, designated K310, K235, and K115, and the length polymorphism designated as K185/175. Polymorphism K310 mapped to chromosome 10, K235 mapped to distal ch2 near Psp, K185/175 mapped to ch10 near CR39, and K115 mapped to distal ch12 near the Ig variable gene cluster. The remaining polymorphism, K360, was not closely linked to previously mapped loci; about 10% of all polymorphisms fall in this class. The polymorphisms are removed from the gel and amplified by PCR. These genetic markers can be used to screen a library of mouse genomic clones or as in situ probes.

12. Detection of Polymorphisms Between Tissues and Strains by AP-PCR of Tissue RNA or cDNA AP-PCR can also be used to detect polymorphisms in gene expression between tissues or strains within a single organism. This allows the identification of a tissue by AP-PCR rather than previous histological or other tissue typing means. Thus, an organ tissue, such as heart, liver, kidney, and the like can readily be distinguished and/or identified by the AP-PCR methods described herein.

Thus, AP-PCR as described herein is performed on total cellular RNA, messenger RNA (mRNA) or cDNA to distinguish differences in RNA populations from different sources. These methods that allow the differential detection of expressed genes are important for tissue typing and for studying gene regulation and differentiation.

For AP-PCR polymorphism tissue typing, total RNA is isolated, cDNA is prepared from the isolated RNA, and the prepared cDNA is used as the template for AP-PCR. There are numerous permutations on the procedure as described further herein.

Total RNA was prepared from various mouse tissues using the guanidium thiocyanate-cesium chloride method of Cirgwin et al., *Biochemistry*, 18:5294–5299, 1979. Other total RNA or mRNA isolation procedures well known in the art could be also be used.

cDNA was then prepared from the isolated RNA as follows. The isolated RNA was dissolved in sterile water at a concentration of 0.02 ug/ul and ethanol-precipitated using 0.3 M sodium acetate, pH 6, and 2.5 volumes ethanol. The resulting pellets were dissolved in sterile water to a concentration of 0.2 ug/ul, heated to 65 C. for 10 min and placed on ice before cDNA synthesis. First strand synthesis of cDNA was performed using 0.5 Units of Moloney reverse transcriptase (Stratagene) in a buffer containing 50 mM Tris pH 8.3, 50 mM KCl, 4 mM MgCl$_2$, 100 uM each dNTP, 20 mM DTT, 1 uM of arbitrary primers KZ and RS described below by admixing these reagents together with from 0.0016 ug to 2.5 ug of the isolated RNA to form a reverse transcriptase primer extension reaction admixture, and maintaining the admixture for 1 hr at 37 C. in a 20 ul reaction volume to form a RNA-DNA hybrid duplex. The arbitrary primers KZ (SEQ ID NO 11) and RS (SEQ ID NO 12) had the nucleotide sequence as follows:

KZ 5'-CCCATGTGTACGCGTGTGGG-3'

RS 5'-GGAAACAGTCATGACCATGA-3'

Second strand cDNA synthesis was also initiated by arbitrary primers KZ and RS by adding each at 1 uM to the resulting first strand synthesis reaction product above together with an equal volume (20 ul) containing 10 mM Tris pH 8.3, 25 mM KCl, 2 mM MgCl$_2$, 2 uCi/ul alpha-[32P]dCTP and 0.1 Unit of Taq polymerase (AmpliTaq; Cetus, Calif.) to form a PCR reaction admixture. The PCR reaction admixture was subjected to one thermocycle of hybridization, primer extension and denaturation according to the temperature profile: 94 C. for 5 min to denature, 40 C. for 5 min for low stringency annealing of primer, and 72 C. for 5 min for primer extension. Alternatively, the low stringency annealing temperature can be as high as 48 C. Thereafter, the PCR reaction admixture was subjected to 30 high stringency thermocycles comprising the temperature profile: 94 C. for 1 min, 60 C. for 1 min and 72 C. for 2 min to form a discrete set of DNA segments corresponding to arbitrarily amplified cDNA.

The resulting set of DNA segments were further analyzed by applying the set of DNA segments to a channel of a separating apparatus and the applied segments were size-separated into bands to form a fingerprint of bands indicative of the RNA population being evaluated. To that end, the amplified DNA segment set in 2.5 ul was admixed with 10 ul of sample buffer containing 80% formamide and dye. The admixture was heated to 65 C. for 15 min and then 2.5 ul of the heated sampled was loaded onto a standard 4% acrylamide-50% Urea sequencing gel prepared in 1×TBE, and electrophoresed at 1500 Volts (V) until the xylene cyanol in the dye reached the bottom of the gel to form a fingerprint pattern to the size-separated DNA segments.

To demonstrate the present embodiment, the total RNA was isolated and analyzed as above using RNA from the various isolated organs from a mouse, namely liver, kidney and heart.

In order to identify the optimum fingerprinting conditions for RNA polymorphisms, several of the reaction parameters were varied in the above procedures, including magnesium concentration, input RNA and cDNA concentrations. The magnesium optimum was determined to be about 4 mM.

Figure 9:
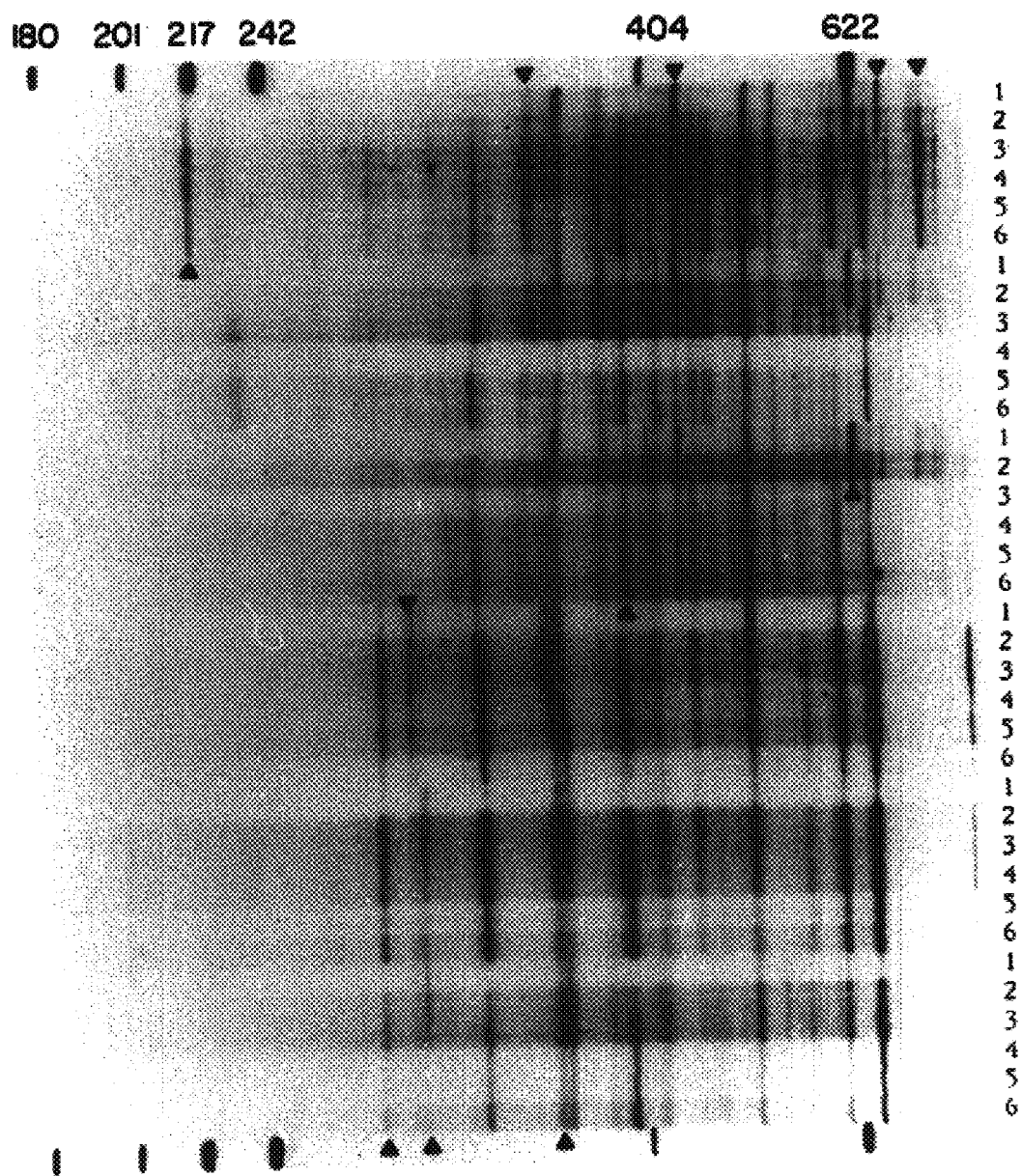
FIG. 9 shows the AP-PCR patterns produced using various amounts of RNA from different mouse tissues as the source of the PCR reaction products. Four cDNA populations were derived using arbitrary primer and total RNA from the kidney and heart of two mice as described in Example 12. Each group of six lanes is for a cDNA derived from 2.5, 1.0, 0.2, 0.04, 0.008, and 0.0016 ug of starting RNA, respectively. Each of the four RNA preparations was amplified by AP-PCR, and some of the resulting polymorphisms between mice or tissues are indicated by the arrow. Molecular weight markers are indicated to the left.

For optimum input RNA determinations, 5 ug of total RNA was used to produce a reaction product from first strand synthesis to produce the first strand cDNA. This first strand synthesis product was serially diluted over a 1500 fold range, corresponding to cDNA from 2.5 ug to 0.0016 ug input RNA, and second strand arbitrarily primed PCR amplification was performed. The resulting fingerprints are shown in FIG. 9. About 10–20 products were detected by each primer from total tissue RNA using this method. The AP-PCR fingerprints produced over this range of input cDNA concentrations were almost identical, except for a few differences at the higher end of the range, such as the band marked "All at about 620 bases in the kidney RNA lanes above 0.04 ug.

Figure 10:
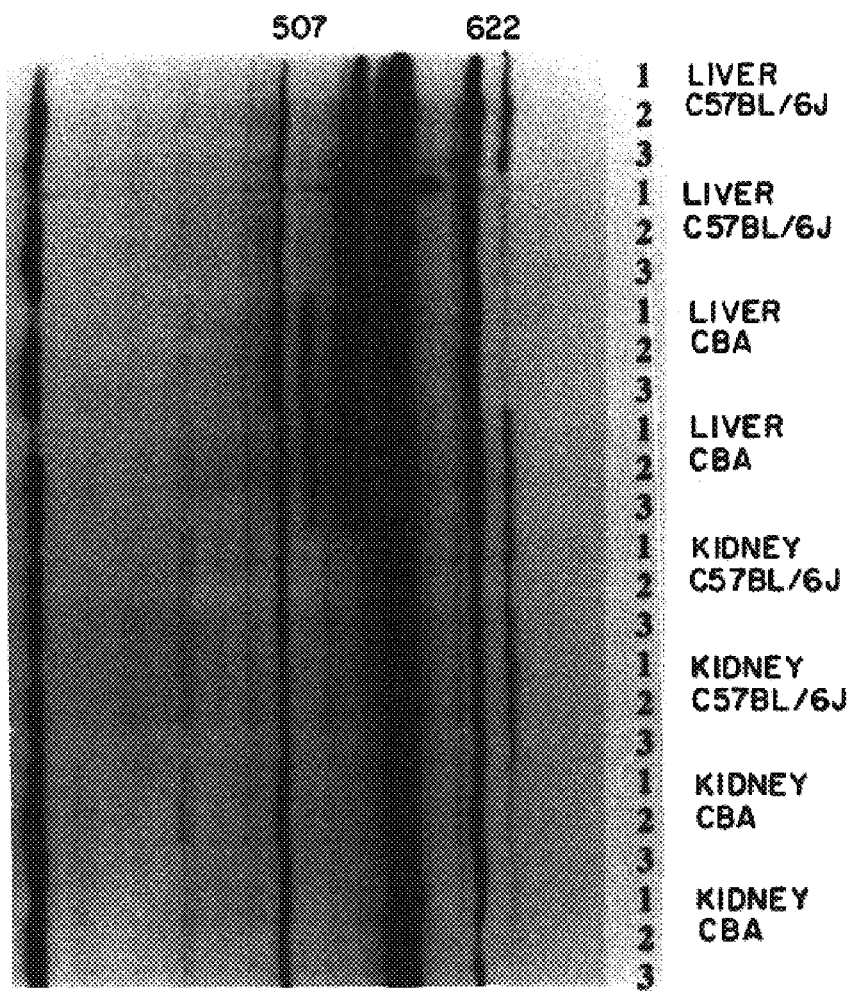
FIG. 10 illustrates RNA AP-PCR as described for FIG. 9, except that the RNA was derived from the liver and kidney of two mice from the inbred lines C57BL/6J and CBA. Each group of three lanes is derived from 0.2, 0.05 and 0.0012 ug of RNA, respectively, as described in Example 12. Molecular weight markers are indicated to the left.

Serial dilution of the total RNA in the range of 2.5 ug to 0.012 ug per 20 ul reaction prior to cDNA synthesis also revealed a broad concentration optimum, over the 500 fold range, as shown in FIG. 10. Thus, the method is reproducible over a wide range of RNA concentrations down to a few nanograms of total RNA.

The AP-PCR RNA fingerprinting method was RNA-dependent, and not due to contaminating genomic DNA. The pattern was insensitive to prior treatment of the input nucleic acid with DNase and was sensitive to RNase.

AP-PCR fingerprinting of genomic DNA requires at least two low stringency annealing steps on denatured DNA, permitting initial priming events to occur in opposite directions, and thereby introducing the primer sequences at two ends and facilitating subsequent high stringency PCR amplification of the bounded sequences. In contrast, in the AP-PCR fingerprinting protocol for RNA, contaminating chromosomal DNA is double stranded during the first strand cDNA synthesis step, and therefore is not able to participate in the first low stringency step. Subsequent to first strand synthesis, only a single round of denaturation and low stringency annealing need occur (with primers greater than 15 bases). Because of this regimen, the arbitrary primer is never introduced into a genomic sequence twice and in opposite directions, and is therefore not an efficient substrate for PCR amplification.

To demonstrate the difference between RNA and DNA AP-PCR, denatured or non-denatured DNA was included in the first strand cDNA reaction. The presence of denatured genomic DNA almost completely eliminates the RNA-dependent pattern, and results in a largely uniform background smear due to the promiscuous priming in the first step under low stringency conditions. However, when 20% of the input nucleic acid is non-denatured genomic DNA, the PCR fingerprints are largely unaffected over a wide range of input RNA concentrations. These results indicate that genomic DNA contamination in the total RNA preparations is tolerated, and does not destroy an interpretable RNA AP-PCR fingerprint.

Because the presence of moderate amounts of dsDNA does not adversely affect the RNA AP-PCR fingerprinting method, the rigorous density centrifugation method used to prepare total RNA is not necessary. The observed insensitivity to moderate dsDNA contamination, combined with the observation that only a few nanograms of RNA is needed per lane allow the application of the method to tissues or cells which are difficult to obtain in large amounts. In cases where many mRNAs are expected to differ, the method reveals a sampling of the different mRNA messages. However, because each primer samples only a small subset of the total RNA population, the method is not appropriate in situations where one is looking for differences in a single message or in a very few number of messages.

Detecting Strain Differences. The AP-PCR RNA fingerprint method can be used to identify genetically distinct strains of the same species. When mouse RNA fingerprints were prepared, although very similar patterns were observed, minor patern differences due to sequence differences were detected. For example, a polymorphism at 217 nucleotides (nt), shown as product F in FIG. 9, revealed a kidney RNA of mouse 1 that is absent in mouse 2 and 3. Similarly, a polymorphism at about 550 nt distinguishes CBA liver from C57BL/6J liver, as shown in FIG. 10.

Thus, the AP-PCR RNA method can be used, for example, to determine if the tissue or cell sample being analyzed is from a particular organism strain, thereby identifying the strain, family and the like genotype.

Furthermore, the method allows the identification of characteristic patterns useful in genetic mapping approaches. If the method is applied to a tissue isolated from a genetic mapping population such as recombinant inbreds, the RNA fingerprint would yield a genetic map for the inbred organism.

Detecting Tissue Differences. The AP-PCR RNA fingerprint method can be used to identify different tissues that reflect tissue-specific gene expression, and can be used as a basis for tissue identification and typing. RNA fingerprints of mouse liver, kidney, and heart tissues revealed numerous differentially expressed genes, as reflected by the patterns seen in both FIGS. 9 and 10.

The differentiation of tissue was also observed where other arbitrary primers were used. For example, a 10 base primer was used to produce a tissue-specific RNA AP-PCR fingerprint. The protocol was altered for the 10 base primer such that the annealing step was at 35 C., and the ramp transition time to 72 C. was increased to 30 seconds.

Selected PCR products produced by different tissue RNA's were isolated from the gel, sequenced, and compared to sequences in published nucleic acid databases to determine the nature of the identified polymorphisms. In comparing the sequences, over 50% of the isolated products possessed previously undescribed nucleic acid sequences, i.e., are new differentially expressed genes.

Thus, the invention also contemplates a cell typing method that generates a discrete set of DNA segments characteristic of a sample of single-stranded RNA from the preselected cell type. The sample of cells can be derived from an organ, a tissue or a cell line. Using the method, one can differentiate distinct tissues within the same organ or different cell types within the same tissue. For example, a tumor cell may be distinguishable from a normal cell of the same tissue due to differences in cell differentiation due to differences in gene expression. Alternatively, one can identify the tissue source for a metastasis by the present methods.

13. Additional Permutations of the AP-PCR Method

Combinations of arbitrary primers and directed primers can also yield useful results.

a. Oligo-dT Primers

For example, in one embodiment, oligo-dT primers were used in the reverse transcriptase step of the RNA AP-PCR fingerprinting method, followed by the use of arbitrary primer at the second low stringency PCR step. This procedure yielded a pattern of PCR products that were, on average, larger than those seen when arbitrary primer is used at both low stringency steps. This protocol is biased against unprocessed RNAs or structural RNAs containing no poly-A stretches, and biased for messenger RNA with poly-A tails.

In a related embodiment, the oligo-dT primer is used in the reverse transcriptase step, and thereafter an aliquot of the first strand synthesis reaction is denatured (or RNAse is used to remove the RNA), forming a single stranded DNA molecule. The single stranded molecule is then subjected to two cycles of low stringency PCR in the presence of an arbitrary primer.

b. AP-PCR Fingerprints Based on a Subset of AP-PCR Products

In another embodiment, applicable to both DNA or RNA AP-PCR fingerprint protocol, the invention describes the use of a second arbitrary primer in the high stringency PCR step which results in the production of a subset of PCR products relative to the first set of discrete PCR products. The advantage of amplifying a subset in an AP-PCR fingerprinting method includes, but is not limited to the simplification of complex patterns.

Subset AP-PCR protocols involve use of a second arbitrary primer or primers in the high stringency PCR step. The second primer (or primers) is identical to the first primer (or primers) used in the low stringency step, except that primer has one or more extra arbitrary bases at the 3' end of the primer (or primers). For example, where a first arbitrary primer (18-mer) is used in the low stringency PCR step, a second primer (18-mer) is used which is identical in sequence to the first primer except that it lacks three bases at the 5' end, and contains an extra 3 arbitrary bases at the 3' end. An exemplary first and second primer (ZF-1, SEQ ID NO 13; and ZF-4, SEQ ID NO 14) have nucleotide sequences as follows:

ZF-1 5'-AAMCCCACCGGAGAGAAA-3'

ZF-4 5'CCCACCGGAGAGAAACCC-3+

The second, high stringency, PCR reaction will only amplify the PCR products formed in the first step due to (1) the high stringency conditions and (2) the use of a primer of exact sequence in the 5' region as the PCR product. However, because of the added 3' sequence, only a subset of PCR products are amplified. Using this method, the size of the subset is controlled by the number of new bases added to the 3' termini of the second primer. Thus, whereas the addition of three bases to the second primer will greatly reduce the PCR product population size in the resulting subset, the addition of two bases, or one base, will progressively increase the size of the resulting subset. Thus the choice of the number of extra bases on the second arbitrary primer directly controls the subset to original set size ratio.

The number of extra bases can be varied widely from one or more bases. However, for practical purposes, the number of extra bases is typically less that about five extra bases due to the dramatic reduction in subset size, and more preferably about 1 to 4 extra bases are included on the 3+ terminus of the second arbitrary primer.

c. AP-PCR RNA Fingerprints Using Combined Steps of First and Second Strand cDNA Synthesis In another embodiment, designed to reduce the number of manipulative steps in an AP-PCR RNA fingerprinting method, the invention contemplates the use of both reverse transcriptase and a thermostable polymerase in the first strand low stringency step. This embodiment removes the step of adding thermostable polymerase after the low stringency reverse transcription step, and renders the procedure more adaptable to automation. This embodiment requires the use of the same arbitrary primer in both the low and high stringency step, but reduces the number of manipulations.

Although the present invention has been described in considerable detail with regard to certain preferred versions thereof, other versions are possible. Therefore, the spirit and scope of the appended claims should not be limited to the descriptions of the preferred version contained herein.

What is claimed is:

1. A method for generating a discrete set of DNA segments characteristic of a sample of a single-stranded RNA, which method comprises:

(a) forming a primer extension reaction admixture by combining, in a primer extension buffer, said RNA sample and at least one first polynucleotide primer from about 10 to about 50 nucleotide bases in length;

(b) maintaining said primer extension reaction under primer extension conditions to produce a hybrid DNA-RNA molecule;

(c) forming a polymerase chain reaction (PCR) admixture by combining, in a PCR buffer, said DNA-RNA hybrid molecule and at least one second polynucleotide primer from about 10 to about 50 nucleotide bases in length, wherein the first and second primer may be the same or different from one another; and (d) subjecting said PCR admixture of (c) to at least one PCR thermocycle, each of said thermocycles comprising hybridization, primer extension, and denaturation phases, said hybridization phase comprising hybridization conditions compatible with arbitrary priming of said DNA-RNA hybrid molecule, thereby producing said set of discrete DNA segments;

(e) contacting, in a PCR buffer, the set of discrete DNA segments formed in (d) with the second primer or primers used in (c) to form a second PCR admixture; and (f) subjecting said second PCR admixture to a plurality of PCR thermocycles, each of said thermocycles including hybridization, primer extension and denaturation phases, said hybridization phase comprising hybridization conditions that do not permit the formation of primer-template duplexes with a substantial degree of mismatching, thereby amplifying said set of discrete DNA segments.

2. The method of claim 1, wherein the at least one PCR thermocycle in (d) comprises a plurality of PCR thermocycles.

3. A method for generating a discrete set of DNA segments characteristic of a sample of a single-stranded RNA, which method comprises:

(a) forming a polymerase chain reaction (PCR) admixture by combining said RNA sample, at least one polynucleotide from about 10 to about 50 nucleotide bases in length, and a PCR buffer that comprises both reverse transcriptase and thermostable DNA polymerase;

(b) maintaining said PCR admixture under reverse transcriptase primer extension conditions to produce a hybrid DNA-RNA molecule;

(c) subjecting said PCR admixture of (b) to at least one PCR thermocycle, each of said thermocycles comprising hybridization, primer extension, and denaturation phases, said hybridization phase comprising hybridization conditions compatible with arbitrary priming of said DNA-RNA hybrid molecule, thereby producing said set of discrete DNA segments;

(d) contacting, in a PCR buffer, the set of discrete DNA segments formed in (c) with the primer or primers used in (a) to form a second PCR admixture; and (e) subjecting said second PCR admixture to a plurality of PCR thermocycles, each of said thermocycles including hybridization, primer extension and denaturation phases, said hybridization phase comprising hybridization conditions that do not permit the formation of primer-template duplexes with a substantial degree of mismatching, thereby amplifying said set of discrete DNA segments.

* * * * *

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

TTGTAAAACG AGGCCAGT                                                    18

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

GGAAACAGCT ATGACCATGA                                                  20

(2) INFORMATION FOR SEQ ID NO:3:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GTAATACGAC TCACTATAG                                                   19

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GCAATTAACC CTCACTAAAG                                                  20

(2) INFORMATION FOR SEQ ID NO:5:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
CCAGCTCGAC ATGGCACRTG TATACATAYG TAAC                          34

(2) INFORMATION FOR SEQ ID NO:6:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GGGGACTAGT AAAACGACGG CCAGT                                    25

(2) INFORMATION FOR SEQ ID NO:7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GAGAGGAGAA GGAGAGAGAA RRRRR                                    25

(2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

CCGGCATCGA TRRRRRRCGA CGGCCAG                                  27

(2) INFORMATION FOR SEQ ID NO:9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

CCGGCATCGA TRRRRRRCGA CGGGCAG                                  27

(2) INFORMATION FOR SEQ ID NO:10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

GAGAGGAGAA GGAGAGGGAA RRRRRR                                   26
```

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

CCCATGTGTA CGCGTGTGGG                                              20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GGAAACAGTC ATGACCATGA                                              20

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

AACCCCACCG GAGAGAAA                                                18

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

CCCACCGGAG AGAAACCC                                                18

(2) INFORMATION FOR SEQ ID NO:15:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: modified_base
        (B) LOCATION: 9
        (D) OTHER INFORMATION: /mod_base= OTHER
            /label= N
            /note= "Where N = X = A, T, G or C"

(xi) SEQUENCE DESCRIPTION: SEQ ID NO:15:

```
GGGCAGGANG                                                              10
```

(2) INFORMATION FOR SEQ ID NO:16:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: modified_base
        (B) LOCATION: 4
        (D) OTHER INFORMATION: /mod_base= OTHER
            /label= N
            /note= "Where N = X = A, T, G or C"

(ix) FEATURE:
        (A) NAME/KEY: modified_base
        (B) LOCATION: 3
        (D) OTHER INFORMATION: /mod_base= OTHER
            /note= "Where N = X = A, T, G or C"

(ix) FEATURE:
        (A) NAME/KEY: modified_base
        (B) LOCATION: 2
        (D) OTHER INFORMATION: /mod_base= OTHER
            /note= "Where X = N = A, T, G or C"

(ix) FEATURE:
        (A) NAME/KEY: modified_base
        (B) LOCATION: 5
        (D) OTHER INFORMATION: /mod_base= OTHER
            /note= "Where X= N= A, T, G or C"

(xi) SEQUENCE DESCRIPTION: SEQ ID NO:16:

```
GNNNNTGGG                                                                9
```